(12) United States Patent
    Cherchi et al.

(10) Patent No.: US 11,633,143 B2
(45) Date of Patent: Apr. 25, 2023

(54) SYSTEMS AND METHODS FOR ASSESSMENT OF OCULAR CYCLOTORSION

(71) Applicant: NORTHWESTERN UNIVERSITY, Evanston, IL (US)

(72) Inventors: Marcello Cherchi, Lincolnwood, IL (US); Amir Vahabikashi, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 1107 days.

(21) Appl. No.: 16/325,689

(22) PCT Filed: Aug. 17, 2017

(86) PCT No.: PCT/US2017/047322
§ 371 (c)(1),
(2) Date: Feb. 14, 2019

(87) PCT Pub. No.: WO2018/035312
PCT Pub. Date: Feb. 22, 2018

(65) Prior Publication Data
US 2019/0209070 A1    Jul. 11, 2019

Related U.S. Application Data

(60) Provisional application No. 62/376,735, filed on Aug. 18, 2016.

(51) Int. Cl.
*A61B 3/113*    (2006.01)
*A61B 3/12*    (2006.01)
(Continued)

(52) U.S. Cl.
CPC .......... *A61B 5/4023* (2013.01); *A61B 3/0083* (2013.01); *A61B 3/113* (2013.01);
(Continued)

(58) Field of Classification Search
CPC ..... A61B 5/4023; A61B 3/0083; A61B 3/113; A61B 3/12; A61B 3/145; A61B 5/4082;
(Continued)

(56) References Cited

U.S. PATENT DOCUMENTS 1,662,670 A * 3/1928 Harter ................... A61B 5/107
                                                33/514
4,256,112 A * 3/1981 Kopf ..................... A61B 6/501
                                                5/640
(Continued)

FOREIGN PATENT DOCUMENTS

WO    2015019034 A1    2/2015

OTHER PUBLICATIONS

United State Patent and Trademark Office (ISA/US), "International Search Report for PCT/US2019/047322", US, dated Dec. 11, 2017.

*Primary Examiner* — Rene T Towa
(74) *Attorney, Agent, or Firm* — Locke Lord LLP; Tim Tingkang Xia, Esq.

(57) ABSTRACT

Systems and methods for assessing ocular cyclotorsion are provided utilizing an inter-aural axis location assembly, with a first gyroscope connected to the inter-aural axis location assembly, and a camera assembly for retinal imaging, with a second gyroscope connected to the camera assembly. A processor is utilized to calculate angles between the disc-foveal line, skull-horizontal axis, and earth-horizontal axis for use in determining ocular cyclotorsion, and the determinations or calculations may be used to generate a diagnostic report that may be provided via an output device.

13 Claims, 16 Drawing Sheets

(51) Int. Cl.
*A61B 3/00* (2006.01)
*A61B 3/14* (2006.01)
*A61B 5/00* (2006.01)
*A61B 5/06* (2006.01)

(52) U.S. Cl.
CPC ............... *A61B 3/12* (2013.01); *A61B 3/145* (2013.01); *A61B 5/4082* (2013.01); *A61B 5/4863* (2013.01); *A61B 5/067* (2013.01); *A61B 2562/0219* (2013.01)

(58) Field of Classification Search
CPC ................. A61B 5/4863; A61B 5/067; A61B 2562/0219; A61B 3/0025
See application file for complete search history.

(56) References Cited

U.S. PATENT DOCUMENTS

| | | | | |
|---|---|---|---|---|
| 5,094,521 | A * | 3/1992 | Jolson | A61B 3/085 351/210 |
| 2003/0223037 | A1 * | 12/2003 | Chernyak | G06F 3/013 351/209 |
| 2006/0087618 | A1 | 4/2006 | Smart et al. | |
| 2011/0152711 | A1 | 6/2011 | Della Santina et al. | |
| 2012/0074168 | A1 * | 3/2012 | Newman | B67D 1/0022 222/1 |
| 2013/0162947 | A1 * | 6/2013 | Spasovski | G06T 7/74 351/246 |
| 2014/0243623 | A1 | 8/2014 | Kersting et al. | |
| 2016/0085299 | A1 * | 3/2016 | Horesh | A61B 3/0025 345/156 |

* cited by examiner

SYSTEMS AND METHODS FOR ASSESSMENT OF OCULAR CYCLOTORSION

CROSS-REFERENCE TO RELATED APPLICATION

This application claims the benefit of priority of U.S. Provisional Patent Application Ser. No. 62/376,735, filed Aug. 18, 2016 and PCT Application Serial No. PCT/US2017/047322, filed Aug. 17, 2017, the disclosure of which is hereby incorporated by reference in its entirety.

FIELD OF THE DISCLOSURE

The present disclosure generally relates to potential diagnosis of several acute disorders of balance in humans, and more particularly to improved systems and methods for expedited assessment of ocular cyclotorsion that may be particularly advantageous in acute settings, such as an emergency room.

This system may be used to improve and expedite in acute settings, such as an emergency rooms or urgent care clinics, inpatient settings, or office settings, screening or diagnosis of several acute disorders of balance, ranging from common but benign (e.g., vestibular neuritis) to rare but life-threatening (e.g., brainstem stroke).

BACKGROUND

Dizziness, vertigo, and other balance related issues are common complaints in clinical settings, particularly in acute settings, such as an emergency room. Balance disorders and dizziness are challenging to rapidly diagnose and objectively assess in a clinic, emergency room or physician's office. Dizziness is a subjective sensation, disrupted balance could have many possible causes, and diagnostic methods using ocular positioning must take into account static versus dynamic abnormalities.

In mammals, the vestibular system consists of the labyrinth (the "balance apparatus" of the inner ear), the vestibular nerve (which transmits "balance signals" from the labyrinth to the brainstem), and the vestibular nuclei in the brainstem (which "process" those balance signals and in turn send new signals to other areas in the body). The output from the vestibular nuclei is sent to many destinations in the nervous system, including the oculomotor nuclei (which control eye movements). For this reason, the study of eye movements affords insight into the function of the vestibular system, both in healthy and in diseased individuals.

It is feasible to study vestibular physiology (the biological functioning of an organism's "balance system") in animals through invasive means such as by placing electrodes into the inner ear or into the brainstem. In humans, such means are generally infeasible, so non-invasive methods of studying vestibular physiology have been developed. Of these non-invasive methods, some are very cumbersome or expensive (such as human sleds [see Lichtenberg 1982], human centrifuges or hydraulic Moog platforms), or are uncomfortable (such as the caloric testing of videonystagmography), and/or would be time consuming (such as the placement of scleral search coils), and therefore, impractical for rapid deployment.

Existing systems and methods have arguably been most successful in understanding the function of the semicircular canals (the parts of the labyrinth that detect rotational acceleration—such as pitch, yaw and roll; see FIG. 1 from Zee 2006) because these structures mediate eye movements in the axial plane (i.e., horizontal rotation around the rostro-caudal axis) and in the sagittal plane (i.e., vertical rotation around the inter-aural axis), which are relatively easy to measure and analyze.

In contrast, the "otolith organs" (the parts of the labyrinth that detect linear acceleration—such as bob, heave and surge, see FIG. 2) have proven more difficult to study because the eye movements that they mediate are harder to measure. Specifically, the utricle and part of the saccule (the two otolith organs in each inner ear) mediate eye movements that involve rotation in the coronal plane (i.e., around the naso-occipital axis; see Diamond and Markham 1981); such eye movements are referred to as "cyclotorsional." Cyclotorsional eye movements have been well described in animal models, as well as in humans following surgical lesions (vestibular neurectomy); see Curthoys and Dai 1991; Curthoys and Halmagyi 1991; Diamond and Markham 1981; Halmagyi and Curthoys 1991. When cyclotorsional eye movements are abnormal, they are sometimes referred to as "cyclodeviation."

Difficulties in measuring ocular cyclotorsion are especially problematic in clinical medicine because ocular cyclotorsion is abnormal in several acute balance disorders that are extremely common (such as vestibular neuritis) or dangerous (such as brainstem stroke; see Biotti 2011) and, distinguishing between these diagnoses is a significant challenge, especially in acute settings.

While there do exist techniques for detecting ocular cyclotorsion "externally" (i.e., by observing the front of the outside of the eyeball), they have specific limitations. There are two general approaches.

The first technique is the scleral search coil technique (see Robinson 1963). Scleral search coils involve placing a contact lens on an individual's eye. The perimeter of the lens contains a wire with a capacitor, functioning as a circuit. An external magnetic field applied intermittently will "charge" this circuit. In the periods when the external magnetic field ceases, the capacitor discharges and the lens circuit creates a magnetic dipole, whose orientation can be detected, thereby rendering the orientation of the eyeball in real time.

The second technique involves image analysis of the iris patterns, which are unique to each individual. This includes comparing images of the iris over time, which enables determination of whether ocular cyclotorsion has occurred (see Schworm 2002).

The main problem with both of these "external" techniques is that they can only detect relative ocular torsion. In other words, they can only determine whether the eyeball at a given point in time has rotated (torsionally) some number of degrees in comparison to a previous position. Thus, these techniques cannot determine the absolute torsional position of the eyeball (actually, the position of the eyeball with respect to the orbit or "eye socket").

The torsional position of the eyeball relative to the orbit can be detected "internally" (i.e., by observing part of the inside of the eyeball) by acquiring images of the retina, because the retina has particular anatomical landmarks that, in healthy individuals, normally lie in a specific orientation with respect to the orbit and with respect to gravity. The landmarks most commonly selected for this purpose are the center of the fundus (also called the optic disc, which is where the optic nerve enters the globe of the eye) and the center of the fovea (the area of the retina with the highest visual acuity). See FIG. 3. In a healthy individual who is upright, a line traversing these two structures should be oriented at a specific range of angles with respect to "earth horizontal" (gravity). This angle (between the disc-foveal line and earth-horizontal) is sometimes referred to as the "disc foveal angle" (see https://www.scienceopen.com/document/vid/0b228e65-e6d6-40ac-ba45-aff4b8e551e2). Although there is modest variability among normal individuals (Williams 1992), the disc foveal angle has been found to be a reliable parameter (Lefevre 2007; see http://www.ncbi.nlm.nih.gov/pubmed/17646749). See FIG. 4 (https//www.scielo.br/scielo.php?pid=S0004-27492014000600010&script=sci_arttext).

Some diseases cause cyclodeviation (i.e, abnormal ocular cyclotorsion). Such abnormalities can be static (i.e., the eyes are abnormally "tilted" even when the head is upright and not moving) or dynamic (i.e., the usual torsion that occurs in synchrony with various head movements is abnormal) (see Diamond and Markham 1981). Retinal imaging in such cases will show ocular cyclodeviation. Examples of retinal photographs showing ocular cyclodeviation are shown in FIGS. 5A-5C. See FIG. 5A (http://www.oft.gu.se/webdianos/torsion/torsion.html), FIG. 5B (Biotti 2011 http://www.ncbi.nih.gove/pubmed/?term=22170943), and FIG. 5C (http://webeye.ophth.uiowa.edu/eyeforum/cases/225-CN-IV-palsy.htm).

Because abnormalities in the disc-foveal angle can be subtle, it is important that its orientation be measured accurately with respect to the skull ("skull-horizontal axis") and with respect to gravity ("earth-horizontal axis"). With respect to determining the skull-horizontal axis, for any reason, likely the most common technique for doing so is to have the individual clench down on a bite plate, such as is shown in FIG. 6, which conforms to what is known as the "occlusal plane," as represented in FIG. 7. However, it should be noted that there is significant variation in the orientation of the occlusal plane in the general population, as shown for example in FIG. 6. Consequently, using a bite plate or bite block is not a reliable method of determining "horizontalness" with respect to the skull. As such, the inventor is not aware of apparatus or methods presently publicly available that account for such variation or that otherwise provide adequate diagnostic capability feasible for use in an acute setting.

Current methods of assessing dizziness include Computed Tomography (CT) scans, Magnetic Resonance Imaging (MRI) scans, and Head-Impulse-Nystagmus-Test-of-Skew (HINTS) exams. Unfortunately, each of these known methods has significant drawbacks. For instance, CT scans are not advisable for patients having sensitivity to radiation. MRI scans are time intensive for the patient, slow down emergency room throughput, and require serial evaluation. HINTS exams have experienced low adoption because they require a skilled examiner and serial evaluation, and a further MRI scan is needed if there is a suspicion of stroke. The shortcomings of the prior art leave a strong but unmet need for better apparatus and methods for expedited assessment of ocular cyclotorsion.

SUMMARY

This disclosure provides apparatus that may be used in systems and methods having advantages in assessing ocular cyclotorsion for the diagnosis of equilibrium or balance disorders associated with dizziness and vertigo. For instance, there is a potential to improve and expedite the screening and diagnosis of balance disorders ranging from common but benign inner ear conditions, such as vestibular neuritis, to rare but life threatening conditions, such as brainstem or posterior fossa stroke that can present with a similar clinical history and physical examination. The characteristics of the systems and methods, such as speed, ease of use for the operator, ease of interpretation for the operator, non-invasiveness, and avoiding discomfort for the patient, make them suitable for deployment in acute settings, such as emergency rooms and outpatient urgent care units, or in clinical, inpatient or office settings.

The system includes two main assemblies for acquiring data, which include an inter-aural axis location assembly and a camera assembly. A first gyroscope is connected to the inter-aural axis location assembly and a second gyroscope is connected to the camera assembly. The inter-aural axis location assembly and a first gyroscope are used to assess the orientation of the head, and therefore, the eyes. The camera assembly and a second gyroscope are used to take images of the eyes, such as retinal images, to detect abnormalities. The inter-aural axis location assembly includes at least one head location surface and at least two ear canal engaging members.

Particularly advantageous versions of the inter-aural axis location assembly include a stabilization tower that is further useful in stabilizing the head of an individual or patient. The inter-aural axis location assembly with a stabilization tower assures a patient's head is absolutely "horizontal" or "level", such that the eye orientation can be absolutely and accurately established, to permit even slight abnormalities to be objectively measured. The stabilization tower may include a second head location surface, so as to provide four points of engagement with the individual, including for example, a forehead rest support, a chinrest support and the at least two ear canal engaging members. This permits one to assess the degree of rotation of the patient's head in the coronal plane, which in essence is the degree to which the head is tilting to the left or right.

The camera assembly is intended to provide retinal images, but could include any one of different available camera modalities suitable for this purpose, such as a slit lamp camera, a laser scanning ophthalmoscope, a confocal camera, or an Optical Coherence Tomography (OCT) camera. Imaging of the retina by the camera assembly is used to identify specific anatomical landmarks of the retina, including the optic disc and the fovea, which reveal the orientation of the eyeball in the coronal plane, in essence whether the eyeball is rotated around the visual axis or line of sight.

The advantageous inter-aural axis location assembly and camera assembly are used to measure eye orientations and abnormalities, as they pertain to the horizon and a processor processes the data collected and when compared to an established calibration, is useful in diagnosing different balance disorders or excluding threatening conditions, such as stroke. The systems and methods combine accurate assessment of head orientation in the coronal plane, via the inter-aural axis location assembly and first gyroscope connected thereto, which specifically reveals head rotation in the coronal plane relative to gravity, with accurate assessment of ocular cyclotorsion through retinal imaging, via a camera assembly and second gyroscope connected thereto, which specifically reveals ocular cyclotorsion or rotation in the coronal plane relative to gravity. Once one knows the degree of coronal rotation of the head with respect to gravity, one can therefrom determine the degree of cyclotorsion of the eye with respect to the head. Since inner ear diseases, such as vestibular neuritis, often manifest with abnormal ocular cyclotorsion, and posterior fossa stroke generally does not affect ocular cyclotorsion, accurate assessment of cyclotorsion can help distinguish these diagnoses.

The advantageous apparatus, system and methods present a solution that uses an imaging technology to characterize specific anatomical configurations within the eye to help identify middle ear conditions, such as vestibular neuritis as the cause of acute dizziness. The advantages are manifested in a non-invasive, rapid procedure, which is comfortable for the patient, and easy for an examiner or technician to administer, while producing results that are easy to interpret. Emergency room physicians enjoy the benefits of faster evaluations, by avoiding brain imaging and specialist consults, ease of use, less patient discomfort, improved diagnostic accuracy, and lower cost, by avoiding MRI scans. Emergency room administrators enjoy the benefits of greater throughput, due to more rapid evaluations, reduced cost through less utilization of brain MRI scans and specialist consults, and reduced liability.

In a first aspect, a system is disclosed for assessing ocular cyclotorsion in an individual, with the system including an inter-aural axis location assembly having at least one head locating surface and at least two ear canal engaging members, a first gyroscope connected to the inter-aural axis location assembly and utilized in measuring a skull-horizontal axis relative to an earth-horizontal axis, a camera assembly located forward of the inter-aural axis location assembly, a second gyroscope connected to the camera assembly and utilized in measuring the earth-horizontal axis and assuring that the camera assembly is completely upright, and wherein the camera assembly is utilized in acquiring images of the eyes of the individual.

In a second aspect, a method of providing an analysis of ocular cyclotorsion of an individual is disclosed, with the method including providing an inter-aural axis location assembly, a camera assembly located forward of the inter-aural axis location assembly, a processor, an input device and an output device. The method further includes using the input device to enter into the processor identifying information relating to the individual, locating the individual's head relative to the inter-aural axis location assembly via engaging at least one head locating surface and at least two ear canal engaging members, wherein a first gyroscope is connected to the inter-aural axis location assembly and provides information to the processor, and a second gyroscope is connected to the camera assembly and provides information to the processor. The method still further includes using the first gyroscope to measure an earth-horizontal axis relative to the inter-aural axis location assembly, using the second gyroscope to measure an earth-horizontal axis relative to the camera assembly, using the camera assembly to record images of the individual's eyes, and processing the measurements from the first and second gyroscopes and the images from the camera assembly to determine ocular cyclotorsion.

In a third aspect, a method of providing an analysis of ocular cyclotorsion of an individual is disclosed, with the method including locating the individual's head relative to an inter-aural axis location assembly having at least one head locating surface and at least two ear canal engaging members, wherein a first gyroscope is connected to the inter-aural axis location assembly and a second gyroscope is connected to a camera assembly, maintaining the individual's head in a specific position and orientation, or moving the head through a plurality of positions and orientations, acquiring a static image or a sequence of images of each retinae of the individual, using a processor to process the images to determine a disc-foveal line as a line traversing a center of the individual's optic disc and a center of the individual's fovea, acquiring a skull-horizontal axis relative to an earth-horizontal axis via the first gyroscope that is connected to the inter-aural axis location assembly, acquiring an earth-horizontal axis via the second gyroscope that is connected to the camera assembly, and using the processor and computerized image recognition to identify the fovea and the optic disc, followed by automated calculation of the angle between each disc-foveal line and (a) the earth-horizontal axis and (b) the skull-horizontal axis, and generating a report of the acquired data.

In a fourth aspect an inter-aural axis location assembly and camera assembly for use in analysis of ocular cyclotorsion are disclosed, wherein the inter-aural axis location assembly further includes a stabilization tower having at least one head locating surface and at least two ear canal engaging members, and the camera assembly further includes a mount located forward of the stabilization tower It is to be understood that both the foregoing general description and the following detailed description are exemplary and provided for purposes of explanation only, and are not restrictive of the subject matter claimed. Further features and objects of the present disclosure will become more fully apparent in the following description of the preferred embodiments and from the appended claims.

It should be understood that the drawings are not to scale. While some details of assessment apparatus, systems and methods of use have not been included, such details are considered to be understandable within the context by those of ordinary skill in the art in light of the present disclosure. It also should be understood that the present invention is not limited to the example embodiments illustrated.

DETAILED DESCRIPTION

Although the following discloses examples of apparatus, systems and methods used in assessing ocular cyclotorsion, persons of ordinary skill in the art will appreciate that the teachings of this disclosure are in no way limited to the specific examples shown. On the contrary, it is contemplated that the teachings of this disclosure may be implemented in alternative configurations and the patent is only limited by the appended claims.

The present disclosure is directed to systems and methods for use in assessing ocular cyclotorsion that: (1) are accurate and reliable; (2) are non-invasive; (3) do not cause excessive discomfort to the individual being examined; (4) can be deployed easily and rapidly; and (5) are low cost. The systems and methods may be particularly useful in diagnosing conditions of individuals who may be complaining of dizziness, vertigo or other symptoms related to imbalance or disequilibrium.

Figure 1:
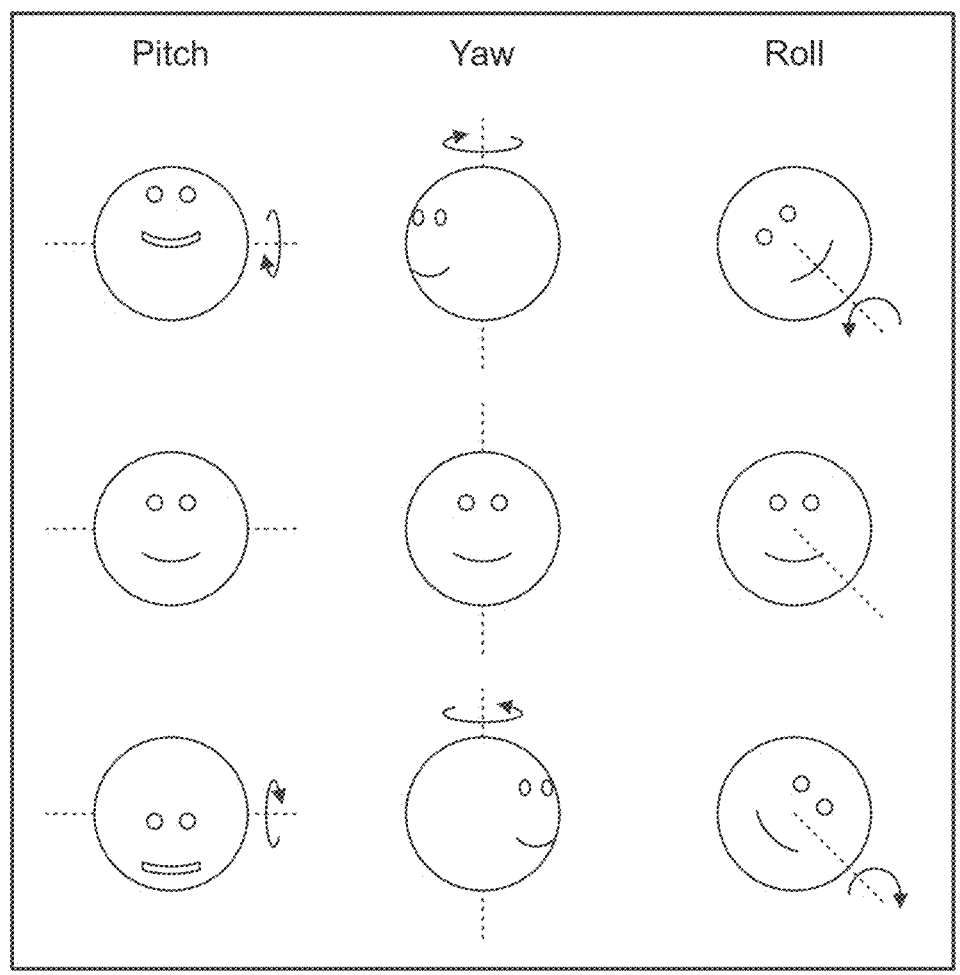
FIG. 1 is diagram that shows conventions for describing head rotations, including vertical (pitch), horizontal (yaw) and torsion (roll).
Figure 2:
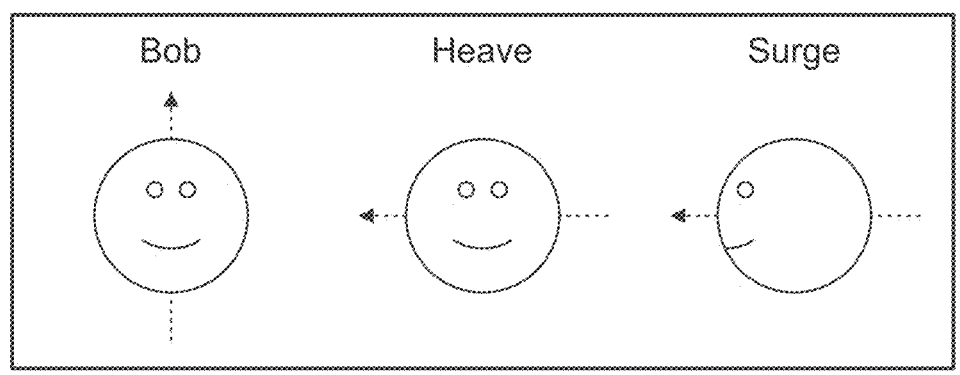
FIG. 2 is diagram that shows conventions for describing head translations, including up and down (bob), side-to-side (heave) and fore and aft (surge).
Figure 3:
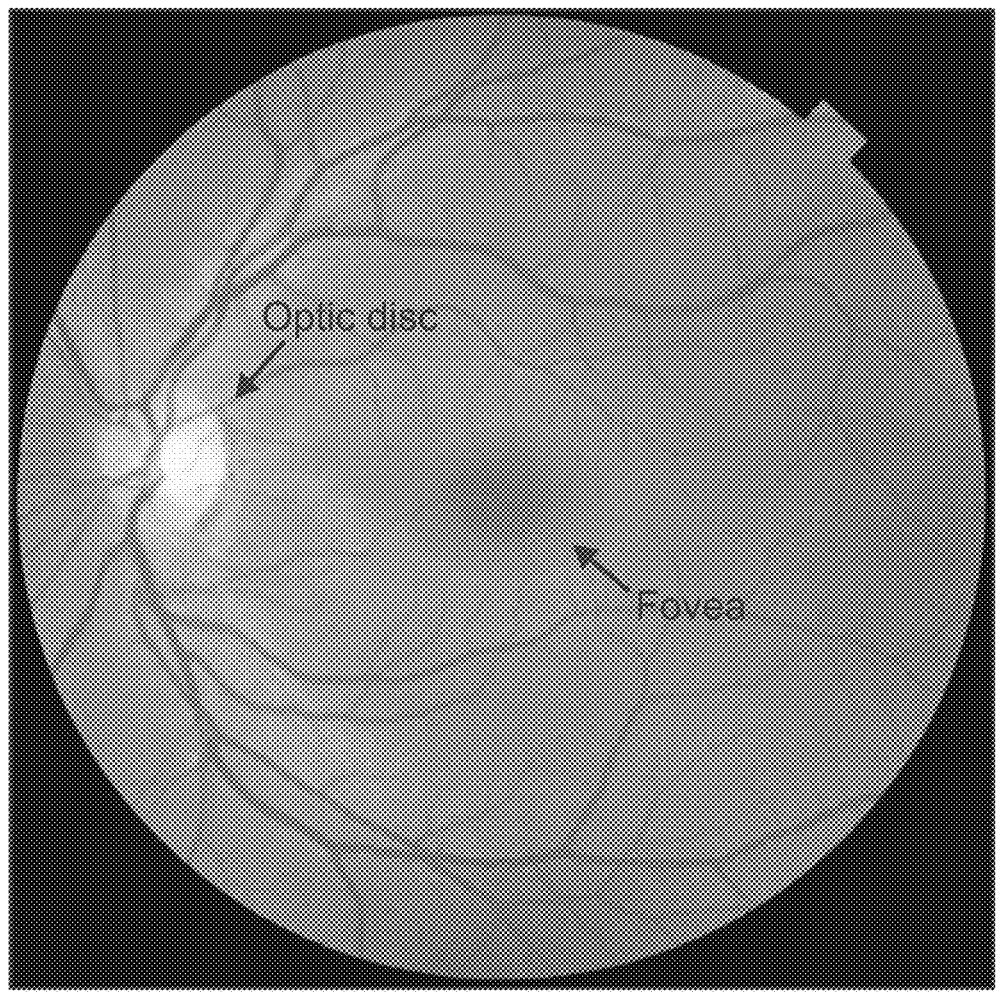
FIG. 3 is an example of a retinal image of an eye identifying the optic disc and fovea.
Figure 4:
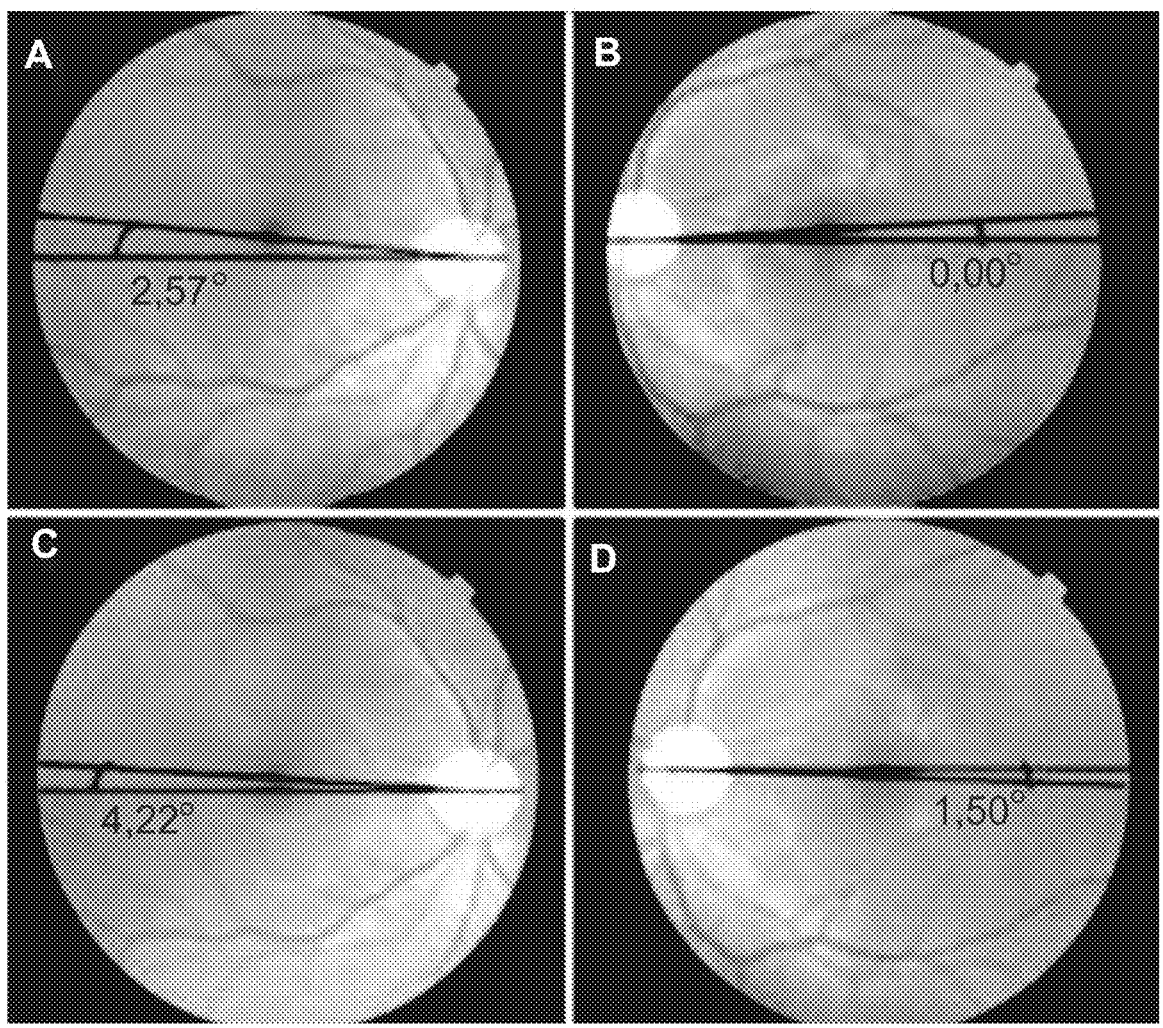
FIG. 4 is an example of internal cyclotorsional position detection via retinal images.
Figure 5A:
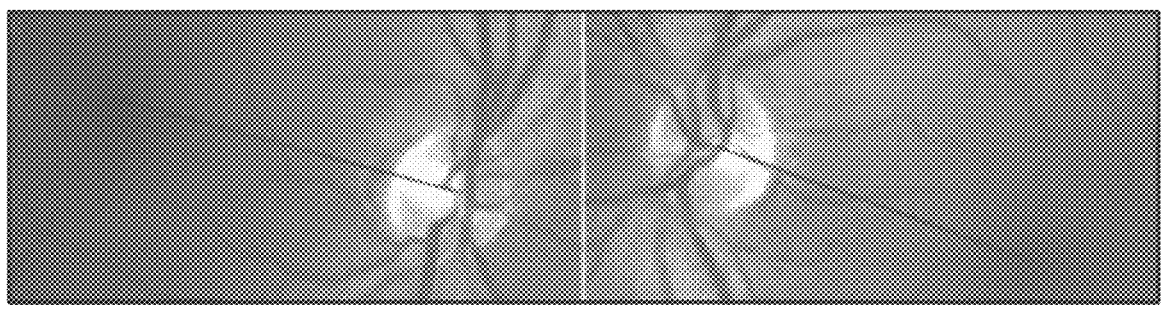
FIG. 5A is a first example of retinal images showing ocular cyclodeviation (abnormal ocular cyclotorsion).
Figure 5B:
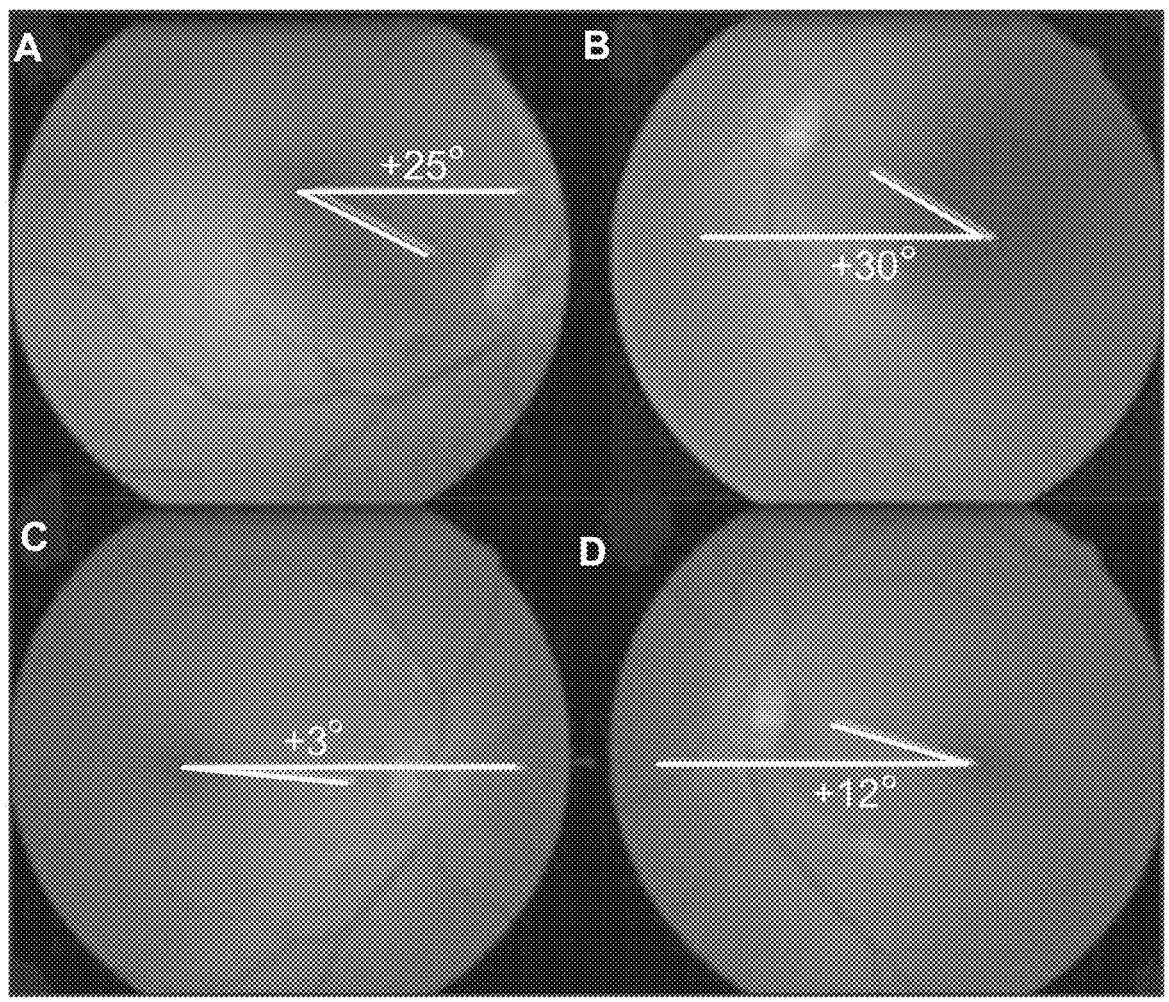
FIG. 5B is a second example of retinal images showing ocular cyclodeviation (abnormal ocular cyclotorsion).
Figure 5C:
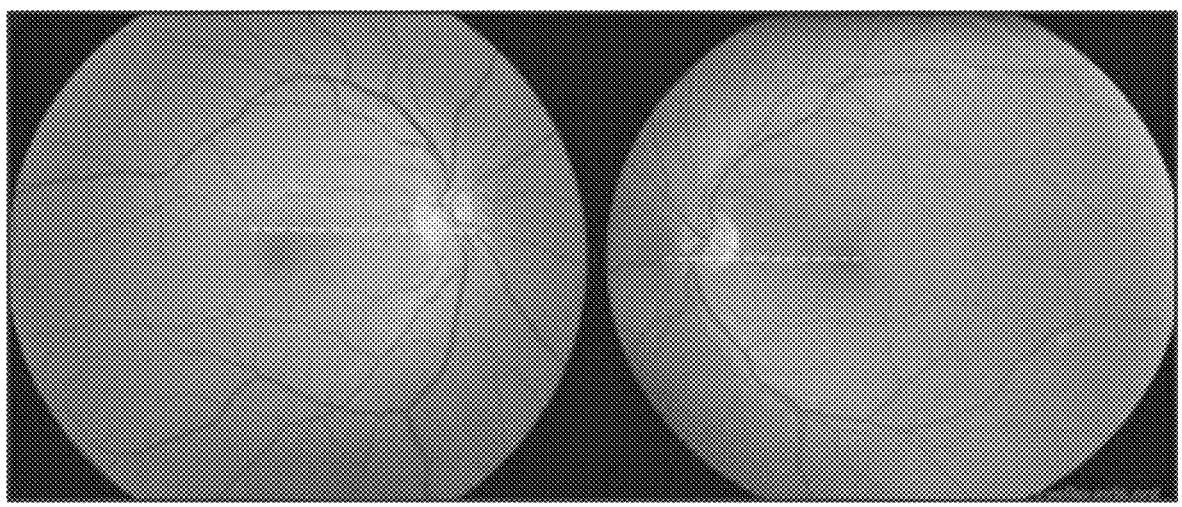
FIG. 5C is a third example of retinal images showing ocular cyclodeviation (abnormal ocular cyclotorsion).
Figure 6:
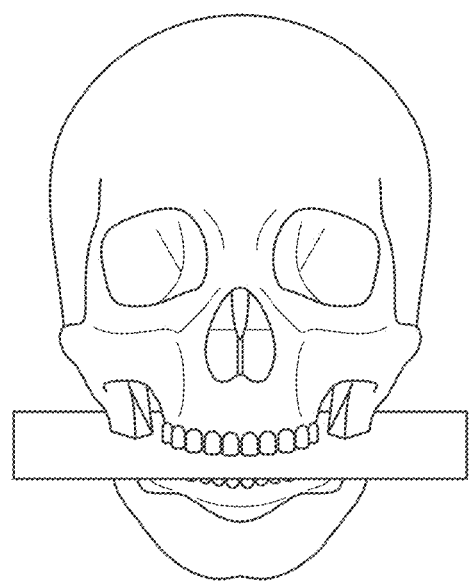
FIG. 6 is sketch showing an example of an individual clenching on a bite plate.
Figure 7:
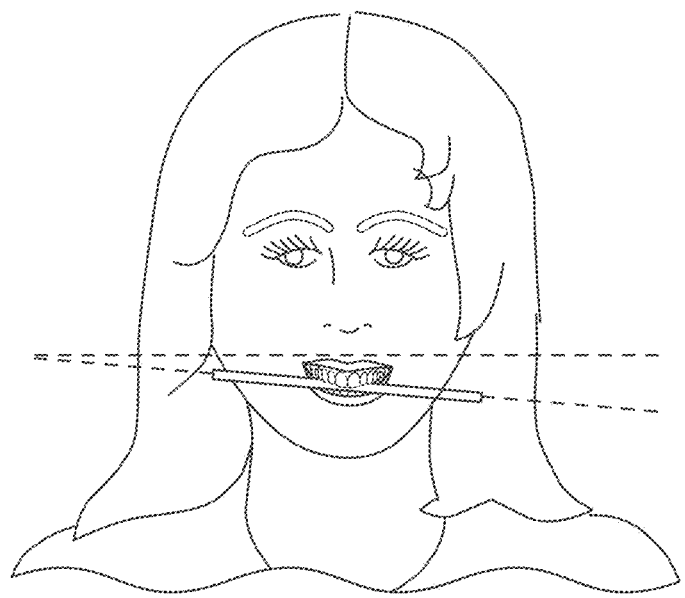
FIG. 7 shows a diagram relating to use of a bite plate in determining an occlusal plane.
Figure 8:
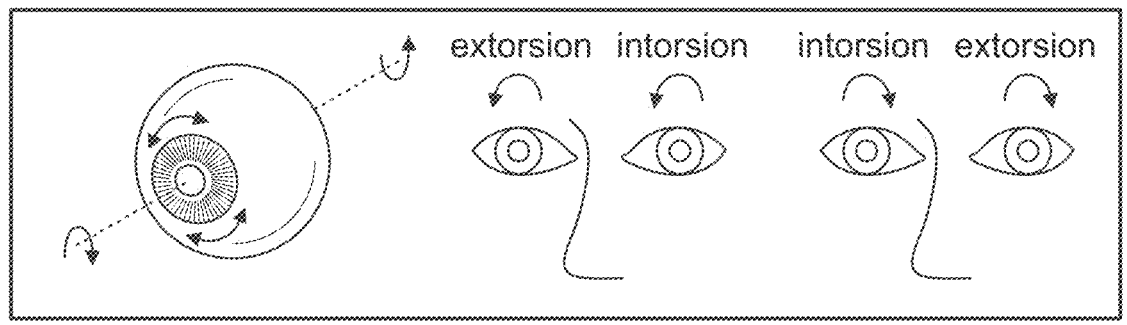
FIG. 8 shows examples of rotation of the eyeballs around the visual axis.
Figure 9:
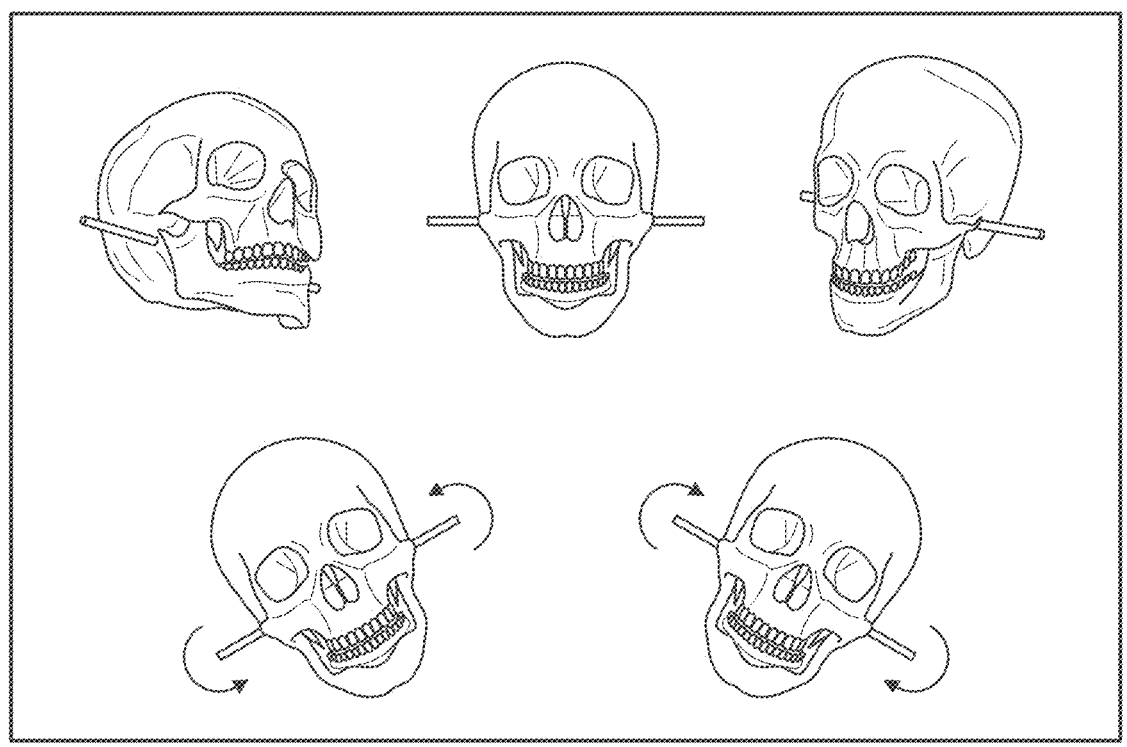
FIG. 9 shows examples of the inter-aural axis relative to rotation of the head in the coronal plane.

In some disorders of balance, the orientation of the eyes (both with respect to the skull and with respect to gravity) is abnormal, but this abnormal orientation cannot be discerned on face-to-face examination since it involves cyclotorsion (rotation of the eyeballs around the visual axis), as shown in FIG. 8. The present disclosure describes systems and methods for assessing cyclotorsion that involves three conceptual steps. First, it is necessary to ascertain the degree of rotation of the head in the coronal plane with respect to gravity. The rotation of the head in the coronal plane is best determined by assessing the inter-aural axis, which is an extremely reliable anatomical landmark, as shown in FIG. 9. The novel inter-aural axis location assemblies described herein, and to which a first gyroscope is connected, take advantage of this reliability. Second, it is necessary to ascertain the degree of ocular cyclotorsion with respect to gravity. The degree of cyclotorsion in a given eye can be assessed by imaging the retina with a suitable camera assembly, to which a second gyroscope is connected, and determining the horizon-disc-foveal angle. This is the angle formed where a line drawn through the optic disc and the macula intersects the line of the horizon, with respect to gravity. A variety of "camera assemblies" as used herein are capable of providing retinal imaging modalities that are suitable for this purpose, including but not limited to, retinal photography, optical coherence tomography and confocal scanning laser ophthalmoscopy. Third, once one knows the degree of coronal rotation of the head with respect to gravity, and the degree of coronal rotation of the eye with respect to gravity, one can therefrom determine the degree of cyclotorsion of the eye with respect to the head. The clinical significance of this is that some acute disorders of balance manifest with particular abnormalities of the horizon-disc-foveal angle, and to the inventor's knowledge, there is no other methodology for studying this that can be conveniently deployed in acute settings, as well as in clinical and office settings.

Turning to the example systems, a first main component that serves as a foundation for the system is provided in the form of an inter-aural axis location assembly, such as is shown in the three examples in FIGS. 10A-10B, 12A-12E and 13A-13D, which will be described further herein. The inter-aural axis (a line running through the center of both external auditory or ear canals) is a very reliable anatomical landmark for assessing skull "horizontalness," and is easily assessed by use of an inter-aural axis location assembly. In addition, a determination of the earth-horizontal axis is accomplished with use of a first gyroscope that is connected to the inter-aural location assembly. The first gyroscope may be any one of a variety of commercially available gyroscopes that may be connected to the inter-aural axis location assembly. A second main component of the system is provided in the form of a camera assembly that is used to provide retinal images, but should be understood as being used herein in a manner in which the camera assembly could include any one of different available camera modalities suitable for this purpose, such as a slit lamp camera, a laser scanning ophthalmoscope, a confocal camera, or an Optical Coherence Tomography (OCT) camera. A commercially available example of a suitable camera can be found in a Spectralis by Heidelberg Engineering (Heidelberg, Germany and Franklin, Mass.). Such a camera is believed to be able to automatically calculate the horizon-disc-foveal angle, which is the angle formed by the intersection of the disc-foveal line and the horizon. However, for purposes of the current invention, it is important that the camera be completely upright, because even a difference of 1-2 degrees can affect whether the result is judged to be pathological or normal. Consequently, a second gyroscope is connected to the camera assembly to permit an operator to know if the camera is completely upright. This essentially can be achieved by tracking the reading from the second gyroscope that is connected to the camera assembly, which should read zero, and if it does not, then the camera assembly needs to be re-leveled, and then by ascertainment of the disc-foveal line. The second gyroscope that is connected to the camera assembly similarly may be of a commercially available type.

In terms of measurement of ocular cyclotorsion with respect to the head of an individual or patient, this can be assessed by (1) determining the rotational orientation of the patient's head in the coronal plane with respect to gravity from the first gyroscope that is connected to the inter-aural axis location assembly when it is applied to the patient's head; (2) determining the rotational orientation (cyclotorsion) of each eye with respect to gravity by comparing the disc-foveal line of each eye (as seen on retinal imaging) with respect to gravity (as detected by a second gyroscope attached to the retinal camera); (3) comparing the rotation of the patient's head in the coronal plane with respect to gravity and the cyclotorsion each eye with respect to gravity, which renders the cyclotorsion of each eye with respect to the patient's head. Precisely measuring static ocular cyclotorsion (cyclotorsional positions at individual times) and dynamic cyclotorsion (cyclotorsional movements in response to head movements) serves as a proxy readout for the function of part of the vestibular system, which governs balance sensation and orientation. Commercially available systems already exist that automatically calculate the disc-foveal angle, such as the Spectralis by Heidelberg Engineering (Heidelberg, Germany and Franklin, Mass.); if a gyroscope is attached to these devices then they could measure ocular cyclotorsion with respect to gravity, but they still would completely lack information about the position of the patient's head in the coronal plane (since they employ no reliable head stabilization apparatus) and therefore they cannot truly measure ocular cyclotorsion with respect to the head.

The present subject matter is fundamentally different from prior apparatus and methods for assessing ocular cyclotorsion in several important respects. First, some prior art used video oculography (image acquisition of the front part of the eyeball), electro-oculographic potentials (measurement of the orientation of the retinal-corneal dipole) or the scleral search coil technique (measurement of a magnetic dipole generated by a special contact lens temporarily worn by the patient) to measure eye movements that rotate the eyeball horizontally (i.e., around the vertical, or rostro-caudal axis) or rotate the eyeball vertically (i.e., around the inter-aural axis). However, as discussed above, while these techniques can assess eyeball rotation in the coronal plane (i.e., around the naso-occipital axis) relative to eyeball position at other points in time, they are unable to assess such rotation "absolutely" (meaning, relative to skull horizontalness), and as such, they cannot measure ocular cyclotorsion relative to the skull. In contrast, the present invention utilizes commercially available retinal imaging systems to assess the disc foveal angle, and in conjunction with the inter-aural axis location assembly, can thereby directly determine ocular cyclotorsion with respect to the head.

Second, while a prior art device may have attempted to stabilize an individual's head by using a bite plate (which conforms to the occlusal plane) and used that as a surrogate reference for the skull-horizontal axis, as discussed above, because jaw malocclusion is quite common, use of the occlusal plane is unreliable for determining the skull-horizontal axis. In contrast, the present invention uses an inter-aural axis location assembly (providing a stable reference through the inter-aural axis), which is a far more reliable anatomical landmark for determination of the skull-horizontal axis. This is further enhanced in the second and third examples of inter-aural axis location assemblies that also include a stabilization tower.

Third, the prior art of which the inventor is aware does not provide any means for assessing the gravity, and therefore cannot compare that axis with eyeball orientation or head orientation. In contrast, the present invention uses gyroscopes for the express purpose of comparing the disk-foveal line with gravity, and head position with respect to gravity, as accuracy is enhanced when one can assure that the camera assembly is in a completely upright position (meaning with respect to the direction in which gravity is acting).

Significantly, the apparatus and methods are designed for use in an acute setting, such as an emergency room, to improve and expedite accurate and reliable diagnosis of several balance disorders, such as distinguishing ones that are common but benign (such as vestibular neuritis) from those that are rare but potentially life-threatening (such as posterior fossa stroke). This further provides a non-invasive method that does not cause discomfort to the individual being examined, can be deployed easily and rapidly, and should be manageable at a relatively low cost, especially relative to the potential to reduce the instances of unnecessary imaging studies (head CT and/or brain MRI) or other more costly and time consuming diagnostic measures.

Thus, ocular cyclotorsion is determined by analysis of data collected while the individual's head is in a specific static position and orientation or via use of a plurality of positions and orientations. An inter-aural axis location assembly having a first gyroscope connected thereto is placed against the individual's head using at least one head locating surface and at least two ear canal engaging members that extend into and engage the individual's ear canals or external auditory canals, so as to be located at and provide stabilization through the inter-aural axis. For example, the at least two ear canal engaging members may engage the ear canals and the at least one head locating surface may be provided by a forehead rest support that engages the forehead of the individual for the purpose of stabilizing the device. As seen in the second and third example inter-aural axis location assemblies, stabilization may be further enhanced by use of an additional head locating surface, such as may be provided by a chinrest support of a stabilization tower.

The specific data collected by the system having an inter-aural axis location assembly, camera assembly and first and second gyroscopes includes: 1) the disc-foveal line (which is the line that passes through the fovea and the center of the optic disc), by retinal imaging with use of retinal imaging equipment, referred to herein as a camera assembly; 2) measurement of the skull-horizontal axis by use of the inter-aural axis location assembly; 3) measurement of the earth-horizontal axis (relative to skull-horizontal axis) by use of the first gyroscope attached to the inter-aural axis location assembly; and 4) measurement of the earth-horizontal axis (relative to the camera assembly) by use of the second gyroscope connected to the camera assembly (in order to assure that the camera assembly is completely upright).

The method therefore comprises use of at least a specialized camera assembly or retinal imaging equipment (connected to the second gyroscope for the purpose of assuring an earth-horizontal orientation of the acquired data) for retinal imaging (which may be capable of capturing static images or real-time video, such as, for example, regular retinal photography, optical coherence tomography, or confocal scanning laser ophthalmoscopy, see Rohrschneider 2004), and an inter-aural axis location assembly to which a first gyroscope is connected. Information recorded by the camera assembly and gyroscopes is provided to a processor, which may include a computer or the like. The information may be provided to the processor via manual data entry, or via networked connection for automated transmission of the data. The processor processes the images using computerized image recognition, which for instance may be provided with the Spectralis by Heidelberg Engineering, and calculates angles between the disc-foveal line, skull-horizontal axis, and earth-horizontal axis for use in determining ocular cyclotorsion, and the determinations or calculations then are used to generate a diagnostic report that may be provided via an output device, such as being displayed on a viewable screen or printed in a hard copy format by a printer.

Stated more specifically, the method of assessment of ocular cyclotorsion of an individual is performed by (1) providing an inter-aural axis location assembly, a camera assembly located forward of the inter-aural axis location assembly, a processor, an input device and an output device; (2) using the input device to enter into the processor identifying information relating to the individual; (3) locating the individual's head relative to the inter-aural axis location assembly via engaging at least one head locating surface and at least two ear canal engaging members, wherein a first gyroscope is connected to the inter-aural axis location assembly and provides information to the processor, and a second gyroscope is connected to the camera assembly and provides information to the processor; (4) using the first gyroscope to measure an earth-horizontal axis relative to the camera assembly; (5) using the camera assembly to record images of the individual's eyes; and (6) processing the measurements from the first and second gyroscopes and the images from the camera assembly to determine ocular cyclotorsion. The method may more specifically include (a) maintaining the individual's head in a specific position and orientation, or moving the head through a plurality of positions and orientations; (b) using a camera assembly (having a position essentially stabilized by a second gyroscope) to acquire a static image (a single image) or real-time video (a sequence of a plurality of images) of each of the two retinae of a subject; (c) using a processor to process those images to determine disk-foveal line (the line traversing the center of the optic disc and the center of the fovea); (d) acquiring the earth-horizontal axis (acquired from the first gyroscope connected to the inter-aural axis location assembly) and comparing it to the skull-horizontal axis (acquired from the inter-aural axis location assembly having been anchored in the individual's ear canals); (e) acquiring the earth-horizontal axis from the second gyroscope that is connected to the camera assembly; (f) using the processor and computerized image recognition for identifying the fovea and the optic disc, followed by automated calculation of the angle between each disc-foveal line and (a) earth-horizontal axis and (b) skull-horizontal axis; and (g) generating a report of the acquired data, which may be provided via an output device such as on a display or by being printed.

The features and advantages of the example apparatus, systems and methods may be better appreciated when considered in connection with the three examples provided in FIGS. 10A-10B, 12A-12E and 13A-13D. The first example shown in FIG. 10A includes an inter-aural axis location assembly 10 having a body 12 that includes a front portion 14 and two side portions 16. The front portion 14 further includes a head locating surface 18 on a forehead rest support 20, which preferably is adjustable at least with respect to its extension toward the forehead of the individual to account for different head sizes. The two side portions 16 further include ear canal engaging members 22, which are adjustable with respect to their extension toward the individual, so as to be able to comfortably engage the respective ear canals of the individual. A first gyroscope 24 is connected to the body 12 for use as described above in recording measurements. The first example inter-aural axis location assembly 10 may be used with other components in a system, such as may be seen in the general diagram shown in FIG. 10B of an example system installation, and in the summary of the method shown in the diagram in FIG. 11.

The examiner E may be seated or standing and may have an input device 30, such as a keyboard, tablet computer, mouse or other suitable input device, to permit the examiner E to enter identifying information regarding the individual or patient P for the assessment of ocular cyclotorsion. As noted in step A of FIG. 11, the information is recorded by a processor 32. In step B, the patient P then engages the inter-aural axis location assembly 10 of FIG. 10A, such as by engaging the head location surface 18 and ear canal engaging members 22. The patient's head is then held in a position or may be rotated in the coronal plane to a specific position, in step C of FIG. 11. A reading from a first gyroscope 24 connected to the inter-aural axis location assembly 10 is recorded by the processor 32, in step D. In step E, imaging of each eye is acquired by a camera assembly 34 located forward of the inter-aural axis location assembly 10, and preferably is pivotable in yaw and pitch. A reading also is taken from a second gyroscope 36 that is connected to the camera assembly 34, and the imaging and gyroscope reading information is recorded by the processor 32. As noted at F, depending on the assessment, the steps of positioning the patient's head and recording the readings from the gyroscopes and the imaging may be repeated for a plurality of different head positions and orientations. The measurements and calculations may be used by the processor 32 to generate a report that may be sent to an output device 38. After acquiring the data, in step G, the patient P disengages from the inter-aural axis location assembly 10. For improved stabilization, a stabilization tower 40 may provide an additional head locating surface, such as is shown in the form of a chinrest support 42.

The second example shown in FIGS. 12A-12E includes an inter-aural axis location assembly 110 having a body 112 that includes a front portion 114 and two side portions 116. The front portion 114 further includes a head locating surface 118 on a forehead rest support 120, which may be adjustable with respect to its extension toward the forehead of the individual to account for different head sizes, but is shown in a fixed position in this example. The two side portions 116 further include ear canal engaging members 122, which are adjustable with respect to their extension toward the individual, so as to be able to comfortably engage the respective ear canals of the individual.

The second example inter-aural axis location assembly 110 further includes a stabilization tower 140 having rear legs 142 and front legs 144, which are connected to a top portion 146 and may be connected to a base 148 or be free standing. The stabilization tower 140 also supports a camera assembly 150 (shown in a simplified manner to focus on the mounting, which would hold a suitable camera device) located forward of the inter-aural axis location assembly. In this example, the camera assembly 150 has a mount 152 that includes a shelf 154 to which is mounted rails 156 extending laterally relative to the tower 140, and which permit the mount 152 and camera assembly 150 to slide horizontally in a lateral direction. The mount 152 also includes rails 158 mounted to the shelf 154 and extending longitudinally or fore and aft relative to the tower 140, and which permit the mount 152 and camera assembly 150 to slide horizontally in a longitudinal direction. The camera assembly 150 and its mount 152 are height adjustable relative to the stabilization tower 140, as the shelf 154 moves along the front legs 144.

The mount 152 also includes a slider base 160 that slides on rails 156, as well as a lower section 162 that is coupled to the slider base 160, with a further upper section 164 that connects to the lower section 162 to secure the camera device. The mount 152 further preferably is configured to allow the camera to be pivotable in yaw and pitch. In this second example, the freedom of movement within the mount 152 is limited by the structure shown in FIG. 12E at the interface between the slider base 160 and the lower section 162 of the mount 152. A second gyroscope 166 is connected to the camera assembly 150 to provide measurements as previously described herein.

The two side portions 116 of the second example inter-aural axis location assembly 110 overlap and slide relative to each other, so as to be able to pivot about rear legs 142 and thereby provide adjustment to the extent of their extension toward the ear canals of an individual. A first gyroscope 168 is connected to the body 112 for use as described above in recording measurements. The stabilization tower 140 of the second example inter-aural axis location assembly 110 may include at least one further head location surface 170, at a chinrest support 172, to provide enhanced stabilization of the individual's head during the assessment. The various components of the inter-aural axis location assembly 110 and camera assembly 150 also may be individually height adjustable, so as to account for differing head and body sizes of various patients.

Figure 10A:
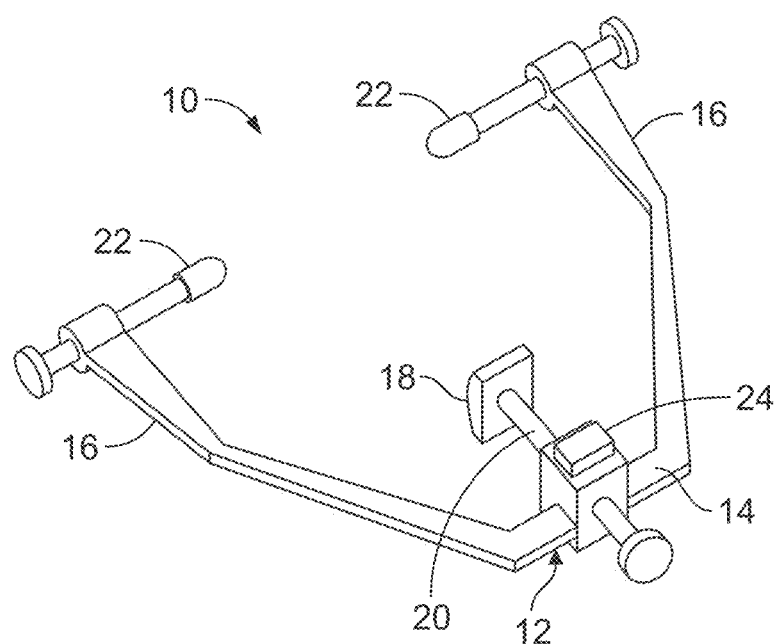
FIG. 10A shows a first example of an inter-aural axis location assembly.
Figure 10B:
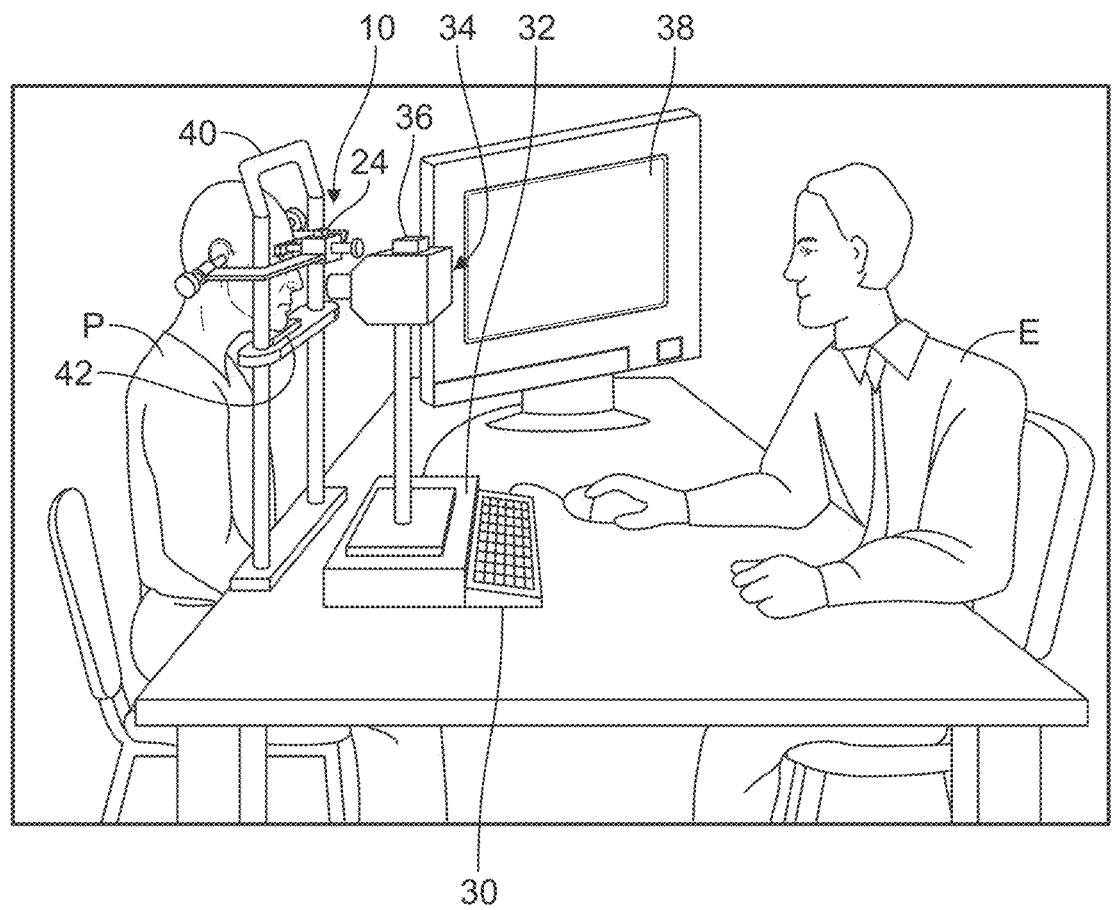
FIG. 10B shows an example system installation for use with the inter-aural location assembly shown in FIG. 10A.
Figure 11:
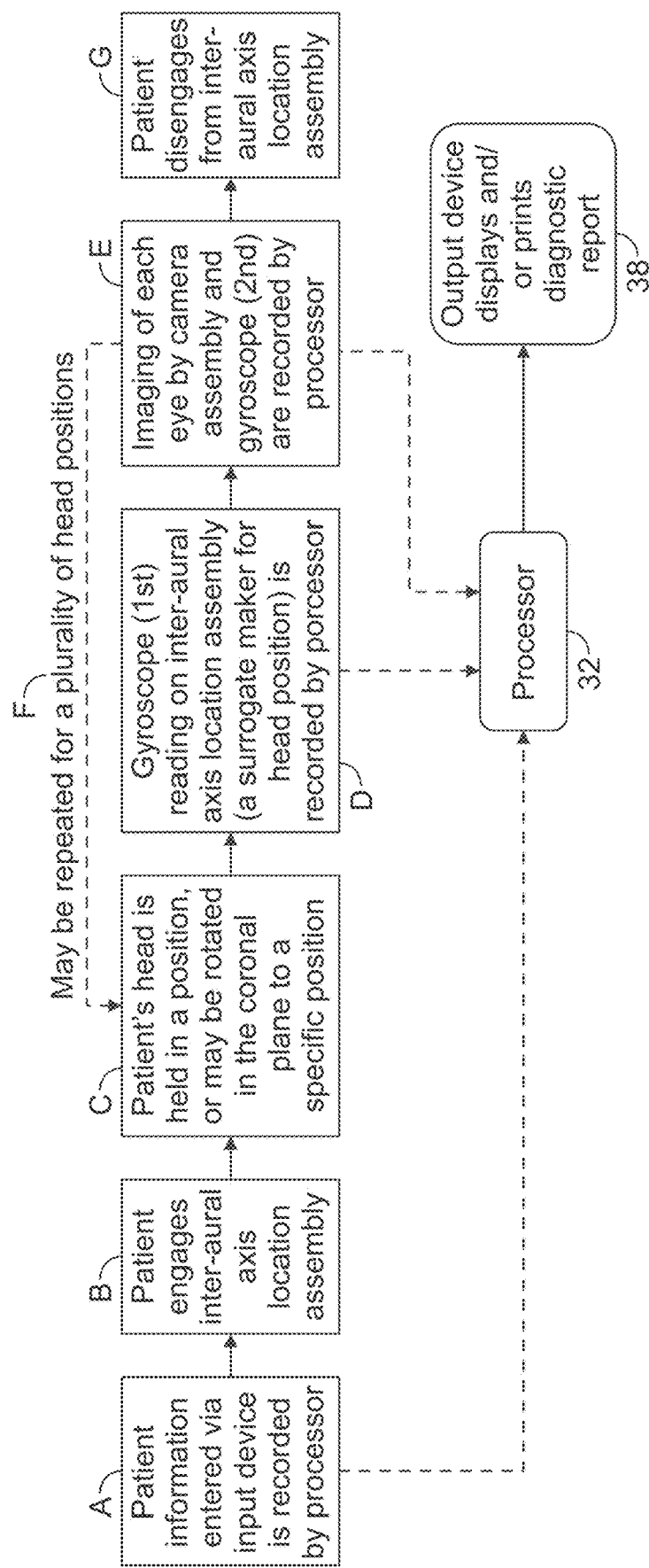
FIG. 11 shows a diagram of a summary of a method of assessing ocular cyclotorsion using an inter-aural axis location assembly, a camera assembly, an input device, a processor and an output device.
Figure 12A:
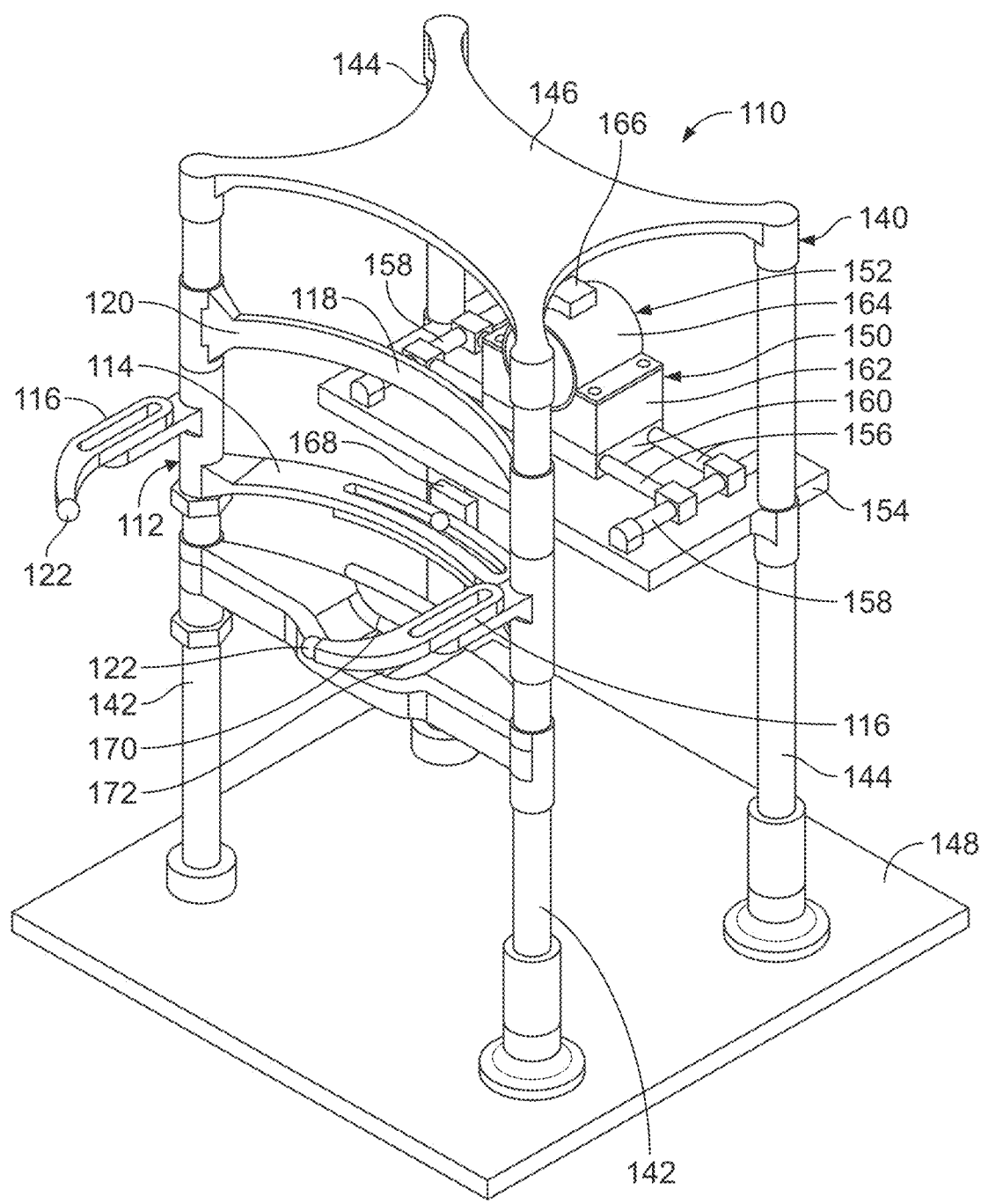
FIG. 12A shows a rear perspective view of a second example of an inter-aural axis location assembly.
Figure 12B:
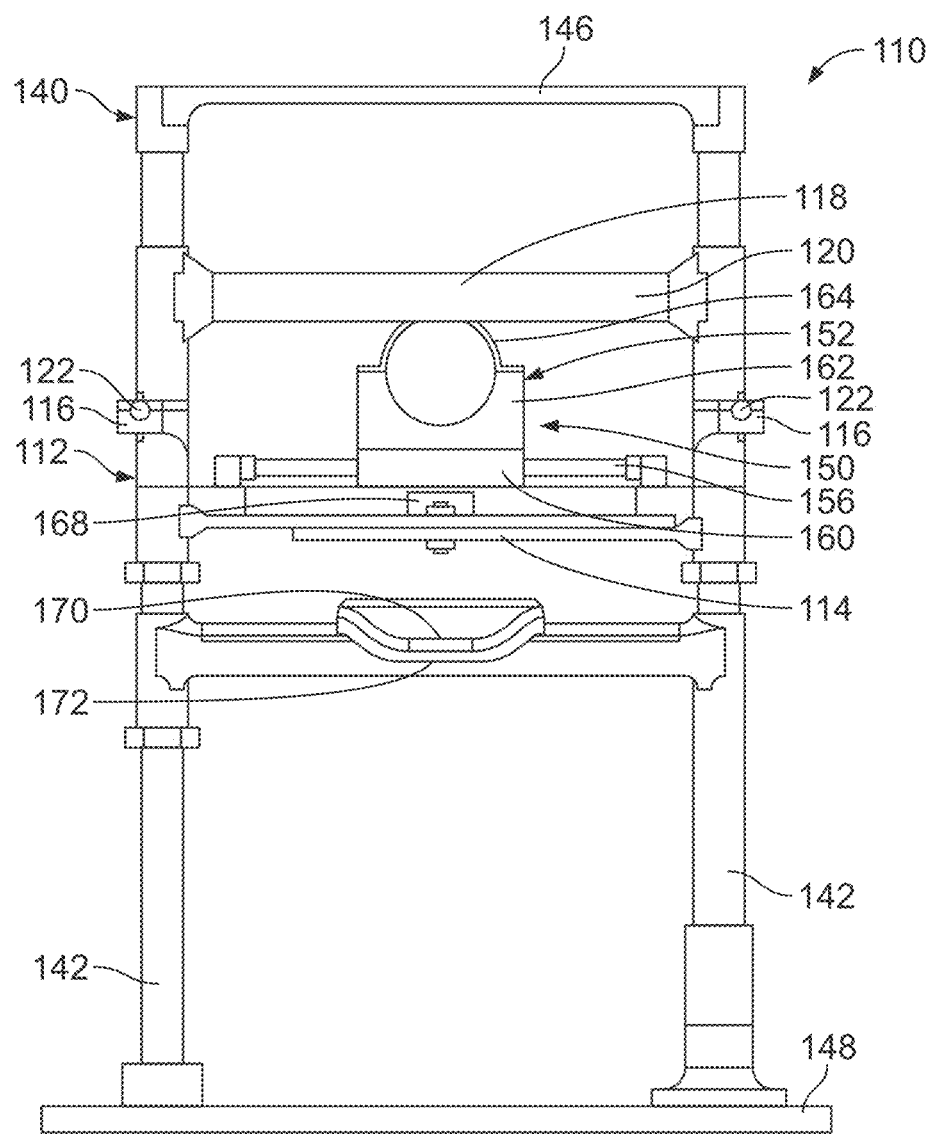
FIG. 12B shows a rear plan view of the second example in FIG. 12A.
Figure 12C:
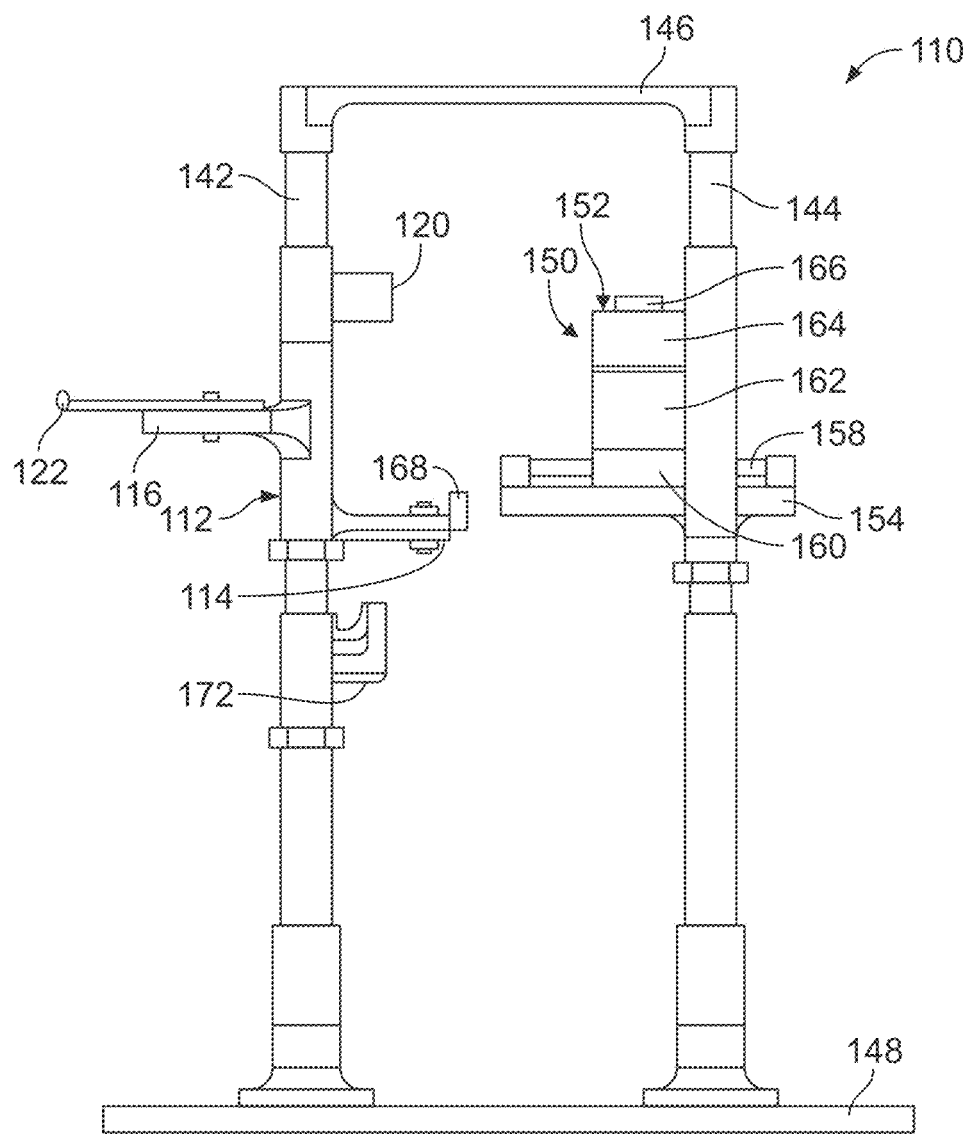
FIG. 12C shows a right side plan view of the second example in FIG. 12A.
Figure 12D:
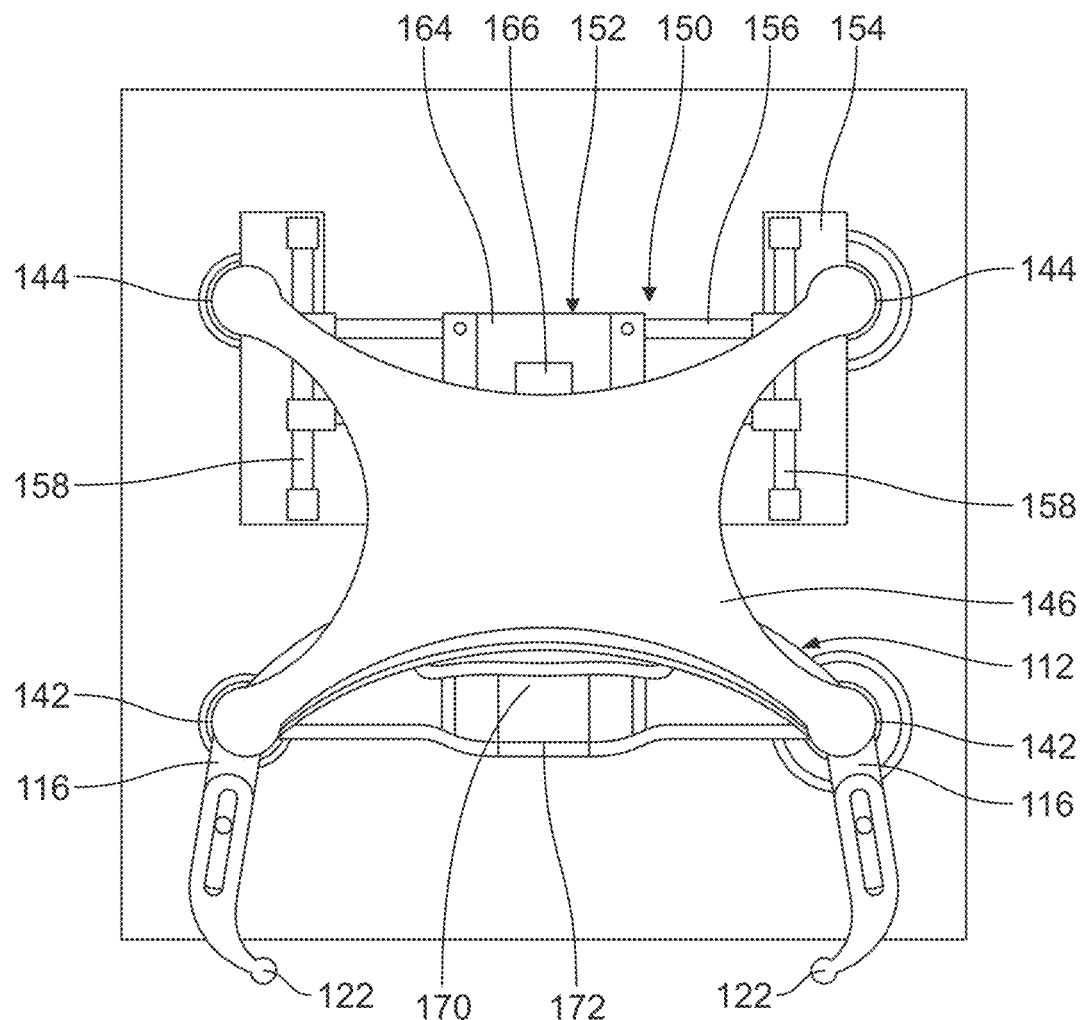
FIG. 12D shows a top plan view of the second example in FIG. 12A.
Figure 12E:
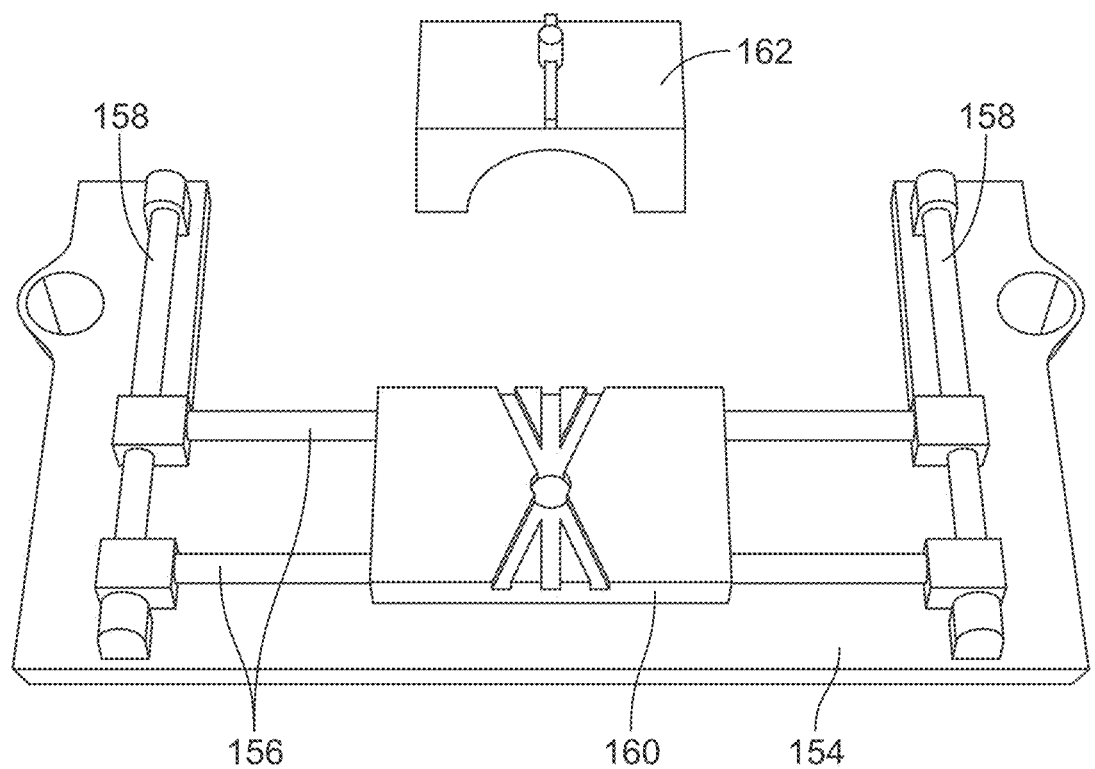
FIG. 12E shows components of the camera mount of the second example in FIG. 12A, which limit pivotable movement.

The second example inter-aural axis location assembly 110 and camera assembly 150 may be used with other components in a system in place of the first example, such as is described above and otherwise set forth in the diagram shown in FIG. 10B of an example system installation, and in the diagram of the method shown in FIG. 11.

The third example shown in FIGS. 13A-13D includes an inter-aural axis location assembly 210 having a body 212 that includes a front portion 214 and two side portions 216. The front portion 214 further includes a head locating surface 218 on a forehead rest support 220, which may be adjustable with respect to its extension toward the forehead of the individual to account for different head sizes. The two side portions 216 further include ear canal engaging members 222, which are adjustable with respect to their extension toward the individual, such as by being threadably or slidingly received by openings in the side portions 216, so as to be able to comfortably engage the respective ear canals of the individual.

The third example inter-aural axis location assembly 210 further includes a stabilization tower 240 having an upstanding frame 242 and a cylindrical fixture 244, which is rotatable relative to the frame 242. The stabilization tower 240 also supports a camera assembly 250 located forward of the inter-aural axis location assembly. In this example, the camera assembly 250 has a mount 252 that supports a camera 254 and includes a base 256 that permits the mount 252 and camera assembly 250 to slide horizontally in a lateral direction, as well as in a longitudinal direction. The mount 252 further preferably is configured to be pivotable in yaw and pitch. A second gyroscope 258 is connected to the camera assembly 250 to provide measurements as described above herein.

Figure 13A:
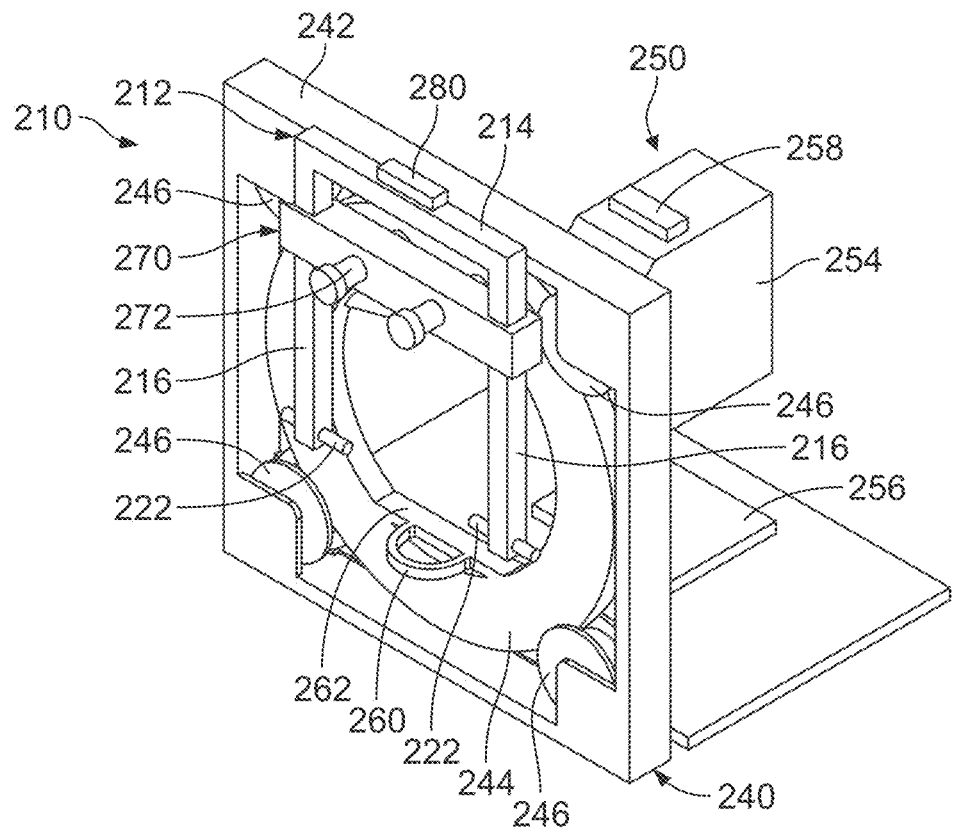
FIG. 13A shows a front perspective view of a third example of an inter-aural axis location assembly with a camera assembly.
Figure 13B:
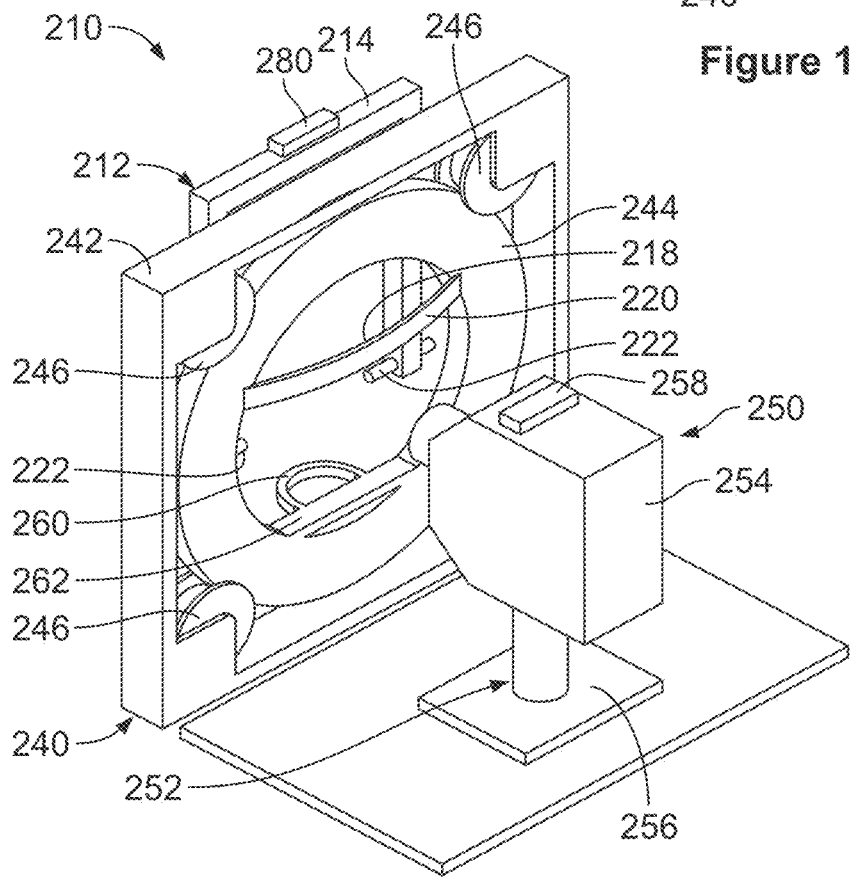
FIG. 13B shows a rear perspective view of the third example in FIG. 13A.
Figure 13C:
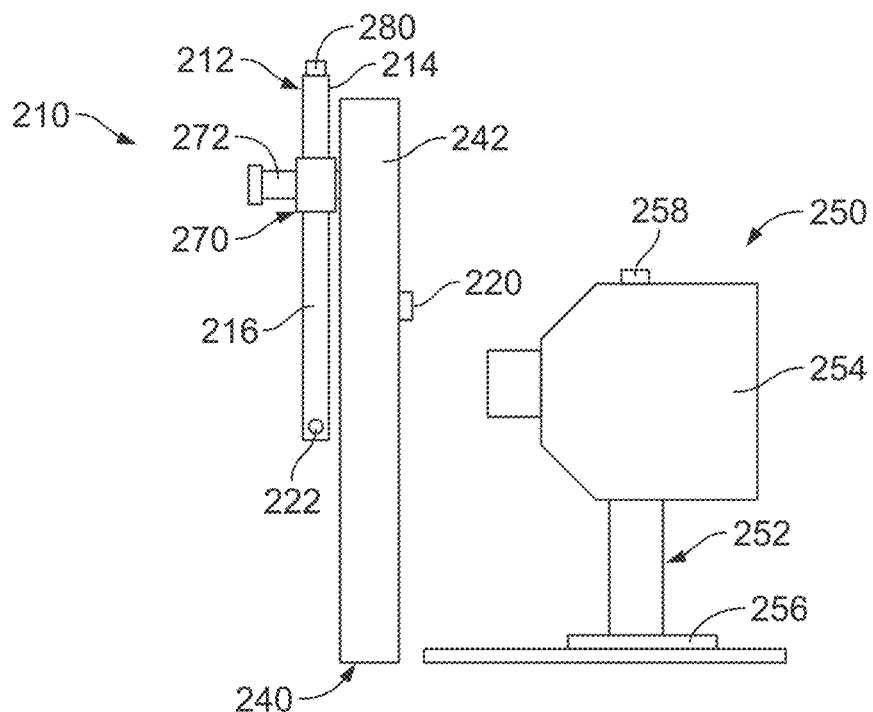
FIG. 13C shows a left side plan view of the third example in FIG. 13A.
Figure 13D:
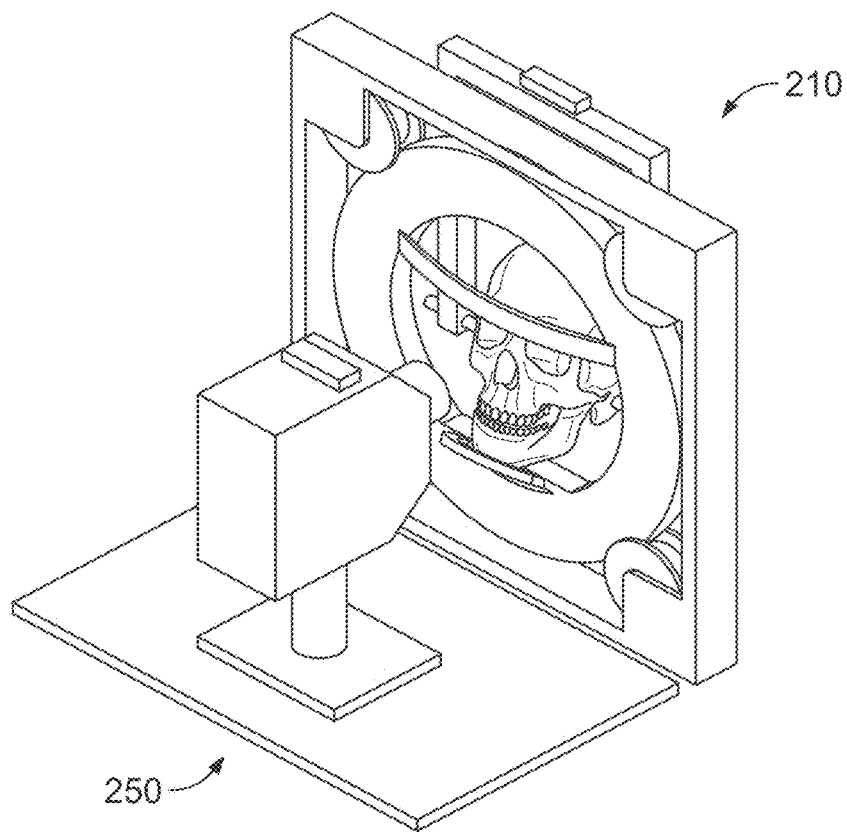
FIG. 13D shows a front perspective view of the third example in FIG. 13A with a skull representing the position of a head of an individual.

The cylindrical fixture 244 may be configured to be rotatable relative to the frame 242 directly, or as shown in FIGS. 13A-13B and 13D, the cylindrical fixture 244 may ride on intermediary members, such as in the form of cylindrical gears 246. This permits movement of the individual's head to various positions and orientations, as may be desired during certain assessments.

The ear canal engaging members 222 of the third example inter-aural axis location assembly 210 are connected to an adjustment assembly 270. The adjustment assembly 270 includes rails 272 extending longitudinally or fore and aft relative to the tower 240, and which permit the side portions 216 and ear canal engaging members 222 to slide horizontally in a longitudinal direction. The adjustment assembly 270 further utilizes the side portions 216 as rails extending vertically relative to the tower 240, and which permit the side portions 216 and ear canal engaging members 222 to slide vertically to comfortably accommodate and engage the ear canals of the individual.

A first gyroscope 280 is connected to the body 212 (as would be the case with the other examples) for use as described above in recording measurements. The stabilization tower 240 of the third example inter-aural axis location assembly 210 may include at least one further head location surface 260, at a chinrest support 262, to provide enhanced stabilization of the individual's head during the assessment. The various components of the inter-aural axis location assembly 210 and camera assembly 250 also may be individually height adjustable, so as to account for differing head and body sizes of various patients. The second example inter-aural axis location assembly 210 and camera assembly 250 may be used with other components in a system in place of the first or second example, such as is described above and otherwise set forth in the diagram shown in FIG. 10B of an example system installation, and in the diagram of the method shown in FIG. 11. FIG. 13D provides an additional view of the third example, which also includes a representation of an individual's head in position for engagement by the inter-aural axis location assembly 210.

The third example may be used in a method of assessing ocular cyclotorsion similar to the prior examples, but includes additional advantages that permit the repeated cycle noted in the summary of the process shown in the diagram of FIG. 11. A method of use for the third example inter-aural axis location assembly 210 and camera assembly 250 could include: (1) having an examiner use an input device to enter the patient's identifying information into the processor; (2) having the patient engage the inter-aural axis location assembly 210 at the head locating surface 260 of the chinrest support 262; (3) the examiner moves the adjustment assembly 270 forward or rearward on the rails 272 until aligned with the patient's ear canals; (4) the examiner moves the adjustment assembly 270 upward or downward on the side portions 216 until the ear canal engaging members 222 are aligned with the patient's ear canals; (5) the examiner slides the ear canal engaging members 222 inward into the patient's ear canals, stabilizing the patient's head and permitting the first gyroscope 280 that is connected to the inter-aural axis location assembly 210 to ascertain the rotational position of the patient's head in the coronal plane; (6) the cylinder 244 then may be rotated to a desired position (depending on what is being studied), thereby also bringing the patient's stabilized head into the selected position, with the first gyroscope 280 recording and providing to the processor the rotation of the patient's head in the coronal plane; (7) the patient is instructed to direct a gaze at a specific target, which may vary depending on what is being studied; (8) the examiner then positions the camera assembly 250 to image the patient's retina in one eye, with the mount 252 for the camera assembly 250 permitting movement upward, downward, forward, rearward, left and right, and rotation about a vertical axis left and right, however, the mount 252 is constrained such that it cannot tilt left or right, because of its completely upright position relative to the direction of gravity must be maintained when acquiring retinal images, as is verified by a reading from the second gyroscope 258; (9) the examiner then uses the camera assembly 250 to acquire the image or series of images (such as via video), which is recorded by the processor; (10) the examiner repeats the positioning of the camera assembly 250 and imaging via the camera assembly 250 to acquire the image or series of images for the patient's second eye; (11) depending on what is being studied the cylindrical fixture 244 and the patient's head may be rotated in the coronal plane by moving the cylindrical fixture 244 to a plurality of angular positions and repeating steps (6) through (10) for each position; (12) the processor produces a report of the acquired results, which may be provided via an output device, such as by being displayed or printed, and in addition to the assessment of ocular cyclotorsion, other information may be displayed, such as normative ranges, prior results from the same patient or other pertinent information.

It will be appreciated that a systems and methods in accordance with the present disclosure may be provided in various configurations. Any variety of suitable materials of construction, configurations, shapes and sizes for the components and methods of connecting the components may be utilized to meet the particular needs and requirements of an end user. It will be apparent to those skilled in the art that various modifications can be made in the design and construction of such diagnostic systems without departing from the scope or spirit of the claimed subject matter and its equivalents, and that the claims are not limited to the preferred embodiments disclosed herein. Also, the following references are referred to within the disclosure.

REFERENCES

Biotti, D. and S. Bidot (2011). "Skew deviation and retinal photography." Neurology 77(24): 2137.

Curthoys, I. S., M. J. Dai and G. M. Halmagyi (1991). "Human ocular torsional position before and after unilateral vestibular neurectomy." Exp Brain Res 85(1): 218-225.

Curthoys, I. S., G. M. Halmagyi and M. J. Dai (1991). "The acute effects of unilateral vestibular neurectomy on sensory and motor tests of human otolithic function." Acta Otolaryngol Suppl 481: 5-10.

Diamond, S. G. and C. H. Markham (1981). "Binocular counterrolling in humans with unilateral labyrinthectomy and in normal controls." Ann N Y Acad Sci 374: 69-79.

Halmagyi, G. M., I. S. Curthoys, T. Brandt and M. Dieterich (1991). "Ocular tilt reaction: clinical sign of vestibular lesion." Acta Otolaryngol Suppl 481: 47-50.

Lefevre F, Leroy K, Delrieu B, Lassale D, Pechereau A. [Study of the optic nerve head-fovea angle with retinophotography in healthy patients] (2007). Journal francais d'ophtalmologie 2007; 30:598-606.

Lichtenberg, B. K., L. R. Young and A. P. Arrott (1982). "Human ocular counterrolling induced by varying linear accelerations." Exp Brain Res 48(1): 127-136.

Robinson D A. A Method of Measuring Eye Movement Using a Scleral Search Coil in a Magnetic Field. IEEE transactions on bio-medical engineering (1963); 10:137-145.

Rohrschneider, K. (2004). "Determination of the location of the fovea on the fundus." Invest Ophthalmol Vis Sci 45(9): 3257-3258.

Schworm, H. D., J. Ygge, T. Pansell and G. Lennerstrand (2002). "Assessment of ocular counterroll during head tilt using binocular video oculography." Invest Ophthalmol Vis Sci 43(3): 662-667.

Williams, T. D. and J. M. Wilkinson (1992). "Position of the fovea centralis with respect to the optic nerve head." Optom Vis Sci 69(5): 369-377.

Zee D S. Pathophysiology of vestibular symptoms and signs: the clinical examination. Continuum (2006); 12:13-32.

The invention claimed is:

1. A system for assessing ocular cyclotorsion in an individual, comprising:
an inter-aural axis location assembly having at least one head locating surface and at least two ear canal engaging members;
a first gyroscope connected to the inter-aural axis location assembly and utilized in measuring a skull-horizontal axis relative to an earth-horizontal axis;
a camera assembly located forward of the inter-aural axis location assembly, wherein the camera assembly comprises a camera device for acquiring images of the eyes of the individual;
a second gyroscope connected to the camera assembly and utilized in measuring the earth-horizontal axis and assuring that the camera assembly is completely upright, verified by a reading from the second gyroscope; and
a processor that receives data from the camera assembly and the first and second gyroscopes, calculates angles between a disc-foveal line, the skull-horizontal axis and the earth-horizontal axis, and determines the ocular cyclotorsion of the individual based on said angles.

2. The system of claim 1, wherein the inter-aural axis location assembly further comprises at least two head locating surfaces and the at least two ear canal engaging members.

3. The system of claim 2, wherein the at least two head locating surfaces further comprise a forehead rest support and a chinrest support.

4. The system of claim 1, wherein the camera assembly images the retina.

5. The system of claim 4, wherein the camera device comprises a retinal camera, optical coherence tomography, a laser scanning ophthalmoscope or a confocal camera.

6. The system of claim 1, wherein the processor generates a diagnostic report.

7. The system of claim 6, further comprising an output device that receives information from the processor and displays or prints the diagnostic report.

8. The system of claim 1, wherein its completely upright position of the camera assembly is achieved by tracking the reading from the second gyroscope that is connected to the camera assembly, and then by ascertainment of the disc-foveal line, wherein when the reading is zero, the camera assembly is completely upright, and when the reading is not zero, the camera assembly is re-leveled until the reading is zero.

9. A method of providing an analysis of ocular cyclotorsion of an individual, comprising:
providing an inter-aural axis location assembly, a camera assembly located proximate the intra-aural axis location assembly, a processor, an input device and an output device, wherein the inter-aural axis location assembly has at least one head locating surface and at least two ear canal engaging members, and the camera assembly comprises a camera device;
using the input device to enter into the processor identifying information relating to the individual;
locating the individual's head relative to the inter-aural axis location assembly via engaging the individual's forehead with the at least one head locating surface and the individual's ear canals with the at least two ear canal engaging members, wherein a first gyroscope is connected to the inter-aural axis location assembly, and a second gyroscope is connected to the camera assembly;
using the first gyroscope to measure a skull-horizontal axis relative to an earth-horizontal axis;
using the second gyroscope to measure the earth-horizontal axis;
using the camera device of the camera assembly to record images of the individual's eyes; and
receiving the measurements from the first and second gyroscopes and the images from the camera assembly, processing the images to determine a disk-foveal line, calculating angles between the disc-foveal line, the skull-horizontal axis and the earth-horizontal axis, and determining the ocular cyclotorsion of the individual based on said angles, by the processor.

10. The method of claim 9, wherein using the camera assembly to record images of the individual's eyes further comprises recording images of each retina.

11. The method of claim 9, further comprising generating a diagnostic report, providing an output device that receives the diagnostic report from the processor and displays or prints the diagnostic report via the output device.

12. The method of claim 9, further comprising using the first gyroscope and inter-aural axis location assembly to determine and record a rotational position of the head in a coronal plane with respect to gravity, using the second gyroscope and images from the camera assembly to determine and record a cyclotorsional position of an eyeball with respect to gravity, and therefrom calculating the cyclotorsional position of the eyeball with respect to the head of the individual.

13. A method of providing an analysis of ocular cyclotorsion of an individual, comprising:

locating the individual's head relative to an inter-aural axis location assembly having at least one head locating surface and at least two ear canal engaging members, wherein a first gyroscope is connected to the inter-aural axis location assembly and a second gyroscope is connected to a camera assembly comprising a camera device;

maintaining the individual's head in a specific position and orientation, or moving the head through a plurality of positions and orientations;

acquiring a static image or a sequence of images of each retinae of the individual via the camera device of the camera assembly;

using a processor to process the acquired static image or the acquired sequence of images to determine a disc-foveal line as a line traversing a center of the individual's optic disc and a center of the individual's fovea;

acquiring a skull-horizontal axis relative to an earth-horizontal axis via the first gyroscope that is connected to the inter-aural axis location assembly;

acquiring an earth-horizontal axis via the second gyroscope that is connected to the camera assembly;

using the processor and computerized image recognition to identify the individual's fovea and the individual's optic disc, calculating angles between the disc-foveal line, the earth-horizontal axis and the skull-horizontal axis; determining the ocular cyclotorsion of the individual based on said angles; and generating a diagnostic report that is provided via an output device.

* * * * *